United States Patent [19]
Koolen et al.

[11] Patent Number: 5,874,526
[45] Date of Patent: Feb. 23, 1999

[54] TOXOPLASMA GONDII ANTIGENS

[75] Inventors: Marcus Joseph Marie Koolen, Houten; Johannes Jozef Wilhelmus De Haard, Michielsgestel, both of Netherlands

[73] Assignee: Akzo Nobel N.V., Arnheim, Netherlands

[21] Appl. No.: 540,118

[22] Filed: Oct. 6, 1995

[30] Foreign Application Priority Data

Jun. 10, 1994 [EP] European Pat. Off. ............ 94202899.4

[51] Int. Cl.$^6$ .............................. C07K 14/45; C07K 7/00; C07K 14/00; A61K 39/02
[52] U.S. Cl. .......................... 530/300; 530/350; 530/325; 530/330; 530/387.1; 530/403; 530/822; 424/184.1; 424/130.1; 424/269.1; 435/7.22; 435/975
[58] Field of Search ...................................... 330/300, 350, 330/325, 330, 387.1, 403, 822; 435/7.22, 975; 424/184.1, 130.1, 269.1

[56] References Cited

U.S. PATENT DOCUMENTS 4,879,213  11/1989  Fox et al. .

FOREIGN PATENT DOCUMENTS 0 301961  2/1989  European Pat. Off. .
2 702491  9/1994  France .

OTHER PUBLICATIONS

L. Lecordier et al., *Mol. Biochem. Parasitol.*, 59:1:143–154, 1993.
H. Charif et al., *Exp. Parasitol.*, 71:1:114–124, 1990.

*Primary Examiner*—Paula J. Hutzell
*Assistant Examiner*—Khalid Masood
*Attorney, Agent, or Firm*—Mary E. Gormley

[57] ABSTRACT

The present invention relates to peptides immunoreactive with antibodies to *Toxoplasma gondii*, nucleic acid sequences encoding these peptides, recombinant vector molecules, comprising these nucleic acid sequences, host cells transformed with the recombinant vector molecule, immunochemical reagents comprising the peptides or antibodies directed against the peptides, a test kit for the detection of *T. gondii* infections as well as a vaccine for the protection against *T. gondii* infections.

In particular the present invention provides peptides comprising part of the amino acid sequence as shown in SEQ ID No.: 1.

A preferred embodiment of the present invention are peptides comprising at least part of the amino acid sequence shown in SEQ ID No.: 3 or 5.

It has been found that the peptides according to the present invention are particularly suitable for diagnosing *T. gondii* infected humans.

6 Claims, 16 Drawing Sheets

```
  1  CCC CCC CCA AAC GAA GTG TCT ACA GCG TGT TTT GCT GTG CAT TGC AGG CTG TTT TAT TTA   60
 61  GAC ATT TTG GCC GCA AAA GAT TTG CTT CGA TGT TTC CGA GCA GGT GAC CTG TTT CGC TTT GAA  120
121  ACA GCA GGA AAA CAG CTT CGT GGT GCC ACG TAG CGT TGT TGG CGA CTA CCT TTT TTT  180
181  CTT GGG GAA GTC GGC ATG GCA CAC GGT GGC ATC CAT CTG AGG CAG AAG CGT AAC TTC  240
       1                  Met Ala His Gly Gly Ile His Leu Arg Gln Lys Arg Asn Phe   14
241  TGT CCT GTA ACT GTC TCC ACA GTT GCT GTA GTC TTT GTA GGT GTA CTC GTC  300
 15  Cys Pro Val Thr Val Ser Thr Val Ala Val Phe Met Gly Val Leu Val   34
301  AAT TCG GGT TTG GGA GTC GGA GTC GCA GAC AGC GCA GAC GTT AAG CAG ACC CCT TCG  360
 35  Asn Ser Gly Leu Gly Val Gly Val Ala Asp Ser Ala Ala Val Lys Gln Thr Pro Ser   54
361  GAA ACC GGT AGC TCG AGC GGT GGC CAA CAG CAG GGG ACC ACT GAA GAT GAT TAT GTC AAC  420
 55  Glu Thr Gly Ser Ser Gly Gly Gln Gln Gln Gly Thr Thr Glu Asp Asp Tyr Val Asn   74
421  TCT TCG GCG ATG GGC GGC GGT TTA GCT GAC GTG CTG CTG ACA ACC TCC GAA  480
 75  Ser Ser Ala Met Gly Gly Gly Leu Ala Asp Val Leu Leu Thr Thr Ser Glu   94
481  GCG GCG GAG GAC GGC GAC GTT GCG AAT GAG CTG GCG AAG GGG TCG GAG GCG  540
 95  Ala Ala Glu Asp Gly Asp Val Ala Asn Glu Leu Ala Lys Gly Lys Ser Glu Ala  114
541  CGT GGC CCG TCG CTC GAG GAA AGA ATC GAA CAG GGC ACA AGA CGA CGT TAC TCC TCT  600
115  Arg Gly Pro Ser Leu Glu Glu Arg Ile Glu Gln Gly Thr Arg Arg Tyr Ser Ser  134
601  GTT CAA GAA CCA CAA CAA AAG GTG CCT AGC GCG AAA ACA CAG CGC CAC AGA CTC ATT  660
135  Val Gln Glu Pro Gln Gln Lys Val Pro Ser Ala Lys Thr Gln Arg His Arg Leu Ile  154
661  GGT GCT GTG TTG GTA GCA TCT GTA TCT GCA ATG CTT ACC GCT TTC TTT CGA AGG ACT  720
155  Gly Ala Val Leu Val Ala Ser Val Ser Ala Met Leu Thr Ala Phe Phe Leu Arg Arg Thr  174
```

FIG. 7A

```
721  GGA CGA CGC TCT CCC CAA GAA CCA TCT GGG GAT GGT GGA AAT GAT GCA GGC AAT AAT   780
175  Gly Arg Arg Ser Pro Gln Glu Pro Ser Gly Asp Gly Gly Gly Asn Asp Ala Gly Asn Asn   194

781  GCT GGG AAC GGT GGG GGG AAT GAA GGC TAC GGA GGT GGC AGA GGT GAA GGA GCC GAG   840
195  Ala Gly Asn Gly Gly Gly Asn Glu Gly Tyr Gly Gly Gly Arg Gly Glu Gly Ala Glu   214

841  GAT GAC AGG CGC CCG TTG CAC CGC GAA CGT GTG AAT GTG TTT GAT TAT TAA AGA TGA AAA   900
215  Asp Asp Arg Arg Pro Leu His Arg Glu Arg Val Asn Val Phe Asp Tyr * * *   231

901  CAG GGG GTC TAT GCG CCA CTG GGG CAC TCT ATG TGT CGA TGC CAT GCA ACG ACC   960

961  GGG AGA GCG GCA CTT ACG TGG ACA GCA GGT CGA AGA ACG TAG GAA TCT GTA CGA ACT GCG CTC CTT   1020

1021 CCA GAA CTT CTG AGG TAG TGT ATC GTC GGC GAT CGC AGG GCT GTA ACG CTC TGA ATG GTT GCG TCT   1080

1081 TTA CAC CTG AGG GTG AAG CCG AAT CTG TCG AGT TAC CAT CTG GCA GTT CGA AGA ATC TTC   1140

1141 CAA AGA ACG GTG AAA ATA AAA AGC AAA GTT TTC GTA AAG TCT GTG GCA GCG ATT CCA GTG AAA AGT   1200

1201 CGG ACT GAA GAT GAA ACA TAA GTA GAG ATA CGA TAA TGC CTC CGA CAC CGC CGG CAT CAC CTG   1260

1261 CGA AGA GAT GAA ACA TAA GTA GAG ATA CGA TAA TGC CTT AAG TGT GAA GCG AAA AGA GTC GCA CAC   1320

1321 CAA GCG TGA CGT TTC AGT CGT TTC GGA AGA TGC TTT AAG TGT GAA GCG AAA AGA GTC GCA CAC   1380

1381 ACG AGA ACG AAT GAG TGT AAA ACA GGG GCC GGA TCA TAC ACC GAC CCG TCG ATG AGG CAG   1440

1441 AGC CGC TGC GCC GAA GCT GCC GCG ATT TGT CAT AAA GTT TTC ACG TGT TTT GTG TTT TGC   1500

1501 GTC GTG ATG CCG GAT TTC CGC TGT TTT CAA AAC TCC ACA CAA GCG CGA AAA ATT   1560

1561 ATG GAA ACG TAT CAT GCG TGG GCT GAA TAC GTT GAA GAA GAA GAA AAA AAA AAA   1614
```

FIG. 7B

AMINO ACID SEQUENCE CLONE #114

RACWRLPFFLGSVGEMAHGGIHLRQKRNFCPVTVST

VAVVFVVFMGVLVNSLGGVAVAADSGGVKQTPSETG

SSGGQQEAVGTTEDYVNSSAMGGGGQGDSLAEDDTTS

EAAEGDVDPFPVLANEGKSEARGPSLEERIEEQGTR

RRYSSVQEPQAKVPSKRTQKRHRLIGAVVLAVSVAM

LTAFFLRRTGRRSPQEPSGDGGGNDAGNNAGNGGNE

GRGYGGGRGEGGAEDDRRPLHPERVNVFDY

FIG. 8

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 230 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Toxoplasma gondii
        ( B ) STRAIN: RH ( v i i ) IMMEDIATE SOURCE:
        ( B ) CLONE: #114

( x i ) SEQUENCE DESCRIPTION: SEQ ID NO: 1:

```
Met  Ala  His  Gly  Gly  Ile  His  Leu  Arg  Gln  Lys  Arg  Asn  Phe  Cys  Pro
 1              5                        10                       15

Val  Thr  Val  Ser  Thr  Val  Ala  Val  Val  Phe  Val  Val  Phe  Met  Gly  Val
               20                        25                       30

Leu  Val  Asn  Ser  Leu  Gly  Gly  Val  Ala  Val  Ala  Ala  Asp  Ser  Gly  Gly
               35                        40                       45

Val  Lys  Gln  Thr  Pro  Ser  Glu  Thr  Gly  Ser  Ser  Gly  Gly  Gln  Gln  Glu
      50                        55                       60

Ala  Val  Gly  Thr  Thr  Glu  Asp  Tyr  Val  Asn  Ser  Ser  Ala  Met  Gly  Gly
65                             70                       75                       80

Gly  Gln  Gly  Asp  Ser  Leu  Ala  Glu  Asp  Asp  Thr  Thr  Ser  Glu  Ala  Ala
                    85                        90                       95

Glu  Gly  Asp  Val  Asp  Pro  Phe  Pro  Val  Leu  Ala  Asn  Glu  Gly  Lys  Ser
               100                       105                      110

Glu  Ala  Arg  Gly  Pro  Ser  Leu  Glu  Glu  Arg  Ile  Glu  Glu  Gln  Gly  Thr
               115                       120                      125

Arg  Arg  Arg  Tyr  Ser  Ser  Val  Gln  Glu  Pro  Gln  Ala  Lys  Val  Pro  Ser
          130                       135                      140

Lys  Arg  Thr  Gln  Lys  Arg  His  Arg  Leu  Ile  Gly  Ala  Val  Val  Leu  Ala
145                       150                      155                      160

Val  Ser  Val  Ala  Met  Leu  Thr  Ala  Phe  Phe  Leu  Arg  Arg  Thr  Gly  Arg
                    165                       170                      175

Arg  Ser  Pro  Gln  Glu  Pro  Ser  Gly  Asp  Gly  Gly  Gly  Asn  Asp  Ala  Gly
                180                       185                      190

Asn  Asn  Ala  Gly  Asn  Gly  Gly  Asn  Glu  Gly  Arg  Gly  Tyr  Gly  Gly  Arg
               195                       200                      205

Gly  Glu  Gly  Gly  Ala  Glu  Asp  Asp  Arg  Arg  Pro  Leu  His  Pro  Glu  Arg
```

|  | 210 | 215 | 220 |  |
|---|---|---|---|---|

Val Asn Val Phe Asp Tyr
225                230

( 2 ) INFORMATION FOR SEQ ID NO: 2:

( i ) SEQUENCE CHARACTERISTICS:
        ( A ) LENGTH: 1617 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Toxoplasma gondii
        ( B ) STRAIN: RH ( v i i ) IMMEDIATE SOURCE:
        ( B ) CLONE: #114

( x i ) SEQUENCE DESCRIPTION: SEQ ID NO: 2:

```
ATTCCCCCC  CAAACGAAGT  GTCTACAGCG  TGTTTTGCTG  TGCATTGCAG  GCTGTTTTAT    60
TTAGACATTT  TGGCCGCAAA  AGATTTGTGT  TTCCGAGCAG  GTGACCTGGG  TCGCTTTTTT   120
GAAACAGCAG  GAAAACAGCT  TCGTGGTGCC  ACGTAGCGTG  CTTGTTGGCG  ACTACCTTTT   180
TTTCTTGGGA  GTGTCGGCGA  AATGGCACAC  GGTGGCATCC  ATCTGAGGCA  GAAGCGTAAC   240
TTCTGTCCTG  TAACTGTCTC  CACAGTTGCT  GTGGTCTTTG  TAGTCTTCAT  GGGTGTACTC   300
GTCAATTCGT  TGGGTGGAGT  CGCTGTCGCA  GCAGACAGCG  GTGGTGTTAA  GCAGACCCCT   360
TCGGAAACCG  GTTCGAGCGG  TGGACAGCAA  GAAGCAGTGG  GGACCACTGA  AGACTATGTC   420
AACTCTTCGG  CGATGGGCGG  TGGCCAAGGC  GACTCGTTAG  CTGAAGATGA  TACAACCTCC   480
GAAGCGGCGG  AGGGCGACGT  TGACCCTTTT  CCCGTGCTGG  CGAATGAGGG  GAAGTCGGAG   540
GCGCGTGGCC  CGTCGCTCGA  GGAAAGAATC  GAAGAACAGG  GCACAAGACG  ACGTTACTCC   600
TCTGTTCAAG  AACCACAAGC  GAAGGTGCCT  AGCAAACGAA  CACAGAAACG  CCACAGACTC   660
ATTGGTGCTG  TGGTGTTGGC  AGTATCTGTG  GCAATGCTTA  CCGCTTTCTT  TCTTCGAAGG   720
ACTGGACGAC  GCTCTCCCCA  AGAACCATCT  GGGGATGGTG  GTGGAAATGA  TGCAGGCAAT   780
AATGCTGGGA  ACGGTGGGAA  TGAAGGCAGA  GGTTACGGAG  GCAGAGGTGA  AGGAGGAGCC   840
GAGGATGACA  GGCGCCCGTT  GCACCCGGAA  CGTGTGAATG  TGTTTGATTA  TTAAAGATGA   900
AAACAGGGGG  TCTATGCGCC  ACTGGGGCAC  TCTATGTCTT  GTAGTCGATG  CCATGCAACG   960
ACCGGGAGAG  CGGCACTGTC  GACGTGGAGA  AGAACGTAGG  AATCTGTACG  AACTGCGCTC  1020
CTTCCAGAAC  TTGGGACGTG  GACAGGTCGA  CATGTGTGAC  GGTCGCGATG  AATGGTTGCG  1080
TCTTTACACC  TGAGGTAGTG  TATCGTCGGC  GATCGCAGGG  CTGTAACGCT  CAGGAGAATC  1140
TTCCAAAGAA  CGGTGAAGCC  GAATCTGTCG  AGTTACCATC  TGGCAGTTGT  GACGTGGTAC  1200
TACCGGACTG  AAATAAAAAG  CAAAGTTTTC  GTAAAGTCTG  TGGCAGCGAT  TCCAGTGAAA  1260
AGTCGAAGAG  ATGAAACATA  AGTAGAGATA  CGATAATGCC  TCCGACACCG  CCGGCATCAC  1320
CTGCAAGCGT  GACGTTTCAG  TCGTGGAAGA  TGCTTTAAGT  GTGAAGCGAA  AAGAGTCGCA  1380
CACACGAGAA  CGAATGAGTG  TAAAACAGGG  GCCGGATCAT  ACACCGACCC  GTCGATGAGG  1440
CAGAGCCGCT  GCGCCGAAGC  TGCCGCGATT  TGTCATAAAG  TTTTCACGTG  TTTTGTGTTT  1500
TGCGTCGTGT  GTATGCCGTG  TCGCGATTTC  GTCTTTCAAA  ACTCCACACA  AGCGCGAAAA  1560
```

ATTATGGAAA CGTATCATGC GTGGGCTGAA TACGATGTTG AAGAAAAAAA AAAAAA    1617

(2) INFORMATION FOR SEQ ID NO: 3:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Toxoplasma gondii
        (B) STRAIN: RH (vii) IMMEDIATE SOURCE:
        (B) CLONE: #114

(xi) SEQUENCE DESCRIPTION: SEQ ID NO: 3:

Asp Thr Thr Ser Glu Ala Ala Glu Gly Asp Val Asp Pro Phe Pro Val
1               5                   10                  15
Leu Ala Asn Glu Gly Lys Ser Glu Ala
            20              25

(2) INFORMATION FOR SEQ ID NO: 4:

(i) SEQUENCE CHARACTERISTICS:
        (A) LENGTH: 75 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Toxoplasma gondii
        (B) STRAIN: RH (vii) IMMEDIATE SOURCE:
        (B) CLONE: #114

(xi) SEQUENCE DESCRIPTION: SEQ ID NO: 4:

GATACAACCT CCGAAGCGGC GGAGGGCGAC GTTGACCCTT TTCCCGTGCT GGCGAATGAG    60

GGGAAGTCGG AGGCG    75

(2) INFORMATION FOR SEQ ID NO: 5:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
        (A) ORGANISM: Toxoplasma gondii (B) STRAIN: RH (xi) SEQUENCE DESCRIPTION: SEQ ID NO: 5:

Asp Val Asp Pro Phe Pro
1               5

(2) INFORMATION FOR SEQ ID NO: 6:

(i) SEQUENCE CHARACTERISTICS:
(A) LENGTH: 18 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Toxoplasma gondii
(B) STRAIN: RH (xi) SEQUENCE DESCRIPTION: SEQ ID NO: 6:

GACGTTGACC CTTTTCCC                                                                18

TOXOPLASMA GONDII ANTIGENS

FIELD OF THE INVENTION

The present invention relates to peptides immunoreactive with antibodies to *Toxoplasma gondii* (to be referred to as *T. gondii* hereinafter), nucleic acid sequences encoding these peptides, recombinant vector molecules comprising these nucleic acid sequences, host cells transformed with the recombinant vector molecule, immunochemical reagents comprising the peptides or antibodies directed against the peptides, a test kit for the detection of *T. gondii* infections as well as a vaccine for the protection against *T. gondii* infections.

BACKGROUND OF THE INVENTION

*T. gondii* is an intracellular protozoan parasite found throughout the world and capable of infecting all species of mammals and all types of cells within a given individual. *T. gondii* is classified as a coccidian with two life cycles, asexual and sexual.

In the asexual stage, *T. gondii* exists in different forms, for instance; tachyzoites, pseudocysts, bradyzoites, and oocysts. The tachyzoite is the obligate intracellular form of *T. gondii* which characterizes acute infection. The infective stage of *T. gondii* for human host cells is the pseudocyst. The pseudocyst has a diameter of 30–100 micrometers and contains hundreds to thousands of infectious units termed bradyzoites. Infection is frequently initiated by ingestion of pseudocysts present in raw or uncooked unfrozen meats. In addition, infection can occur by ingestion of oocysts in the faeces of cats experiencing active intestinal infection. Infections may also be acquired through blood or leukocyte transfusion, by organ transplantation or by transplacental transmission during pregnancy (Wilson et al., J. Exp. Med. 151, 328–346, 1980). The wall of either the pseudocyst or the oocyst is broken down in the small intestine by host digestive enzymes releasing the bradyzoites or sporozoites, respectively, which then penetrate the columnar epithelium. It is probable that bradyzoites or sporozoites reach the liver by the hematogenous route where they are ingested by Kupffer cells. Once inside a cell, the organisms are referred to as tachyzoites. Liver parenchymal cells also become infected (Kranenbühl & Remington, Immun. of Parasitic Infections; eds. Cohen, S., Warren, K. S. London: Blackwell Scientific Publications pp. 356–421, 1982; Remington & Kranenbühl, Immun. of Human Infection, part II, Edited by Nahmias, A. J., O'Reilly, R. J. New York, Plenum Medical Book Company, pp. 327–371, 1982).

Replication immediately follows entry into host cells. In the host, macrophages transport bradyzoites throughout the body. The bradyzoites survive and replicate within the macrophage parasitophorous vacuole by preventing the fusion of lysosomes with it. Replication results in the lysis of the host cell. Organisms are phagocytosed by new macrophages or other cell types and repeat the cycle.

The sexual stage of *T. gondii* occurs only in feline hosts (Miller et al., J. Parasitology, 58, p. 928–937, 1972). The intermediate host (e.g., mouse) becomes infected by ingesting either oocysts or pseudocysts. The mouse develops pseudocysts throughout its own tissues. The cat becomes infected when it eats infected meat (e.g., rodent tissues) containing the pseudocysts or ingests oocysts. Bradyzoites or sporozoites penetrate columnar epithelial cells and differentiate into merozoites. Following replication, merozoites rupture infected epithelial cells and infect adjacent ones. Some merozoites differentiate into pre-sex cells termed macrogametocytes (female form) and microgametocytes (male form). The microgametocytes fuse with macrogametocytes, forming zygotes termed oocysts (Dubey & Frenkel, J. Protozool. 19:155–177, 1972). Oocysts enter lumen of the small intestine and are defecated. Each oocyst sporulates in the soil, producing eight infectious sporozoites, the infectious stage for the intermediate host.

The bradyzoite is the form that encysts approximately 8–10 days after acquisition in vivo and characterizes the chronic, latent phase of infection. Thus, the bradyzoite form is the only stage that has the ability to initiate the enteroepithelial cycle.

*T. gondii* induces a mild or unapparent disease in healthy adults but causes a severe disease, toxoplasmosis, or even death in congenitally infected children and in immunocompromised patients. Primary infection of pregnant women occurs in European countries with frequencies between 0.2 and 1.0%. In approximately 40–50% of the cases, the unborn child is infected. Infection in the fetus during pregnancy will (in approximately 10% of the cases) lead to neonatal death or a severely multi-handicapped child, but in 90% of the cases the child will be born with an asymptomatic, latent infection (Desmonts and Couvreur, Ann. Pediatr. 1984, 31, 805–809; Alford et al. Bull. NY Acad. Med. 1974, 50, 160–181). Up to 85% of the patients with latent congenital toxoplasmosis will develop significant sequelae including one or more episodes of active retinochoroiditis. Other clinical symptoms are inflammation, lymphadenitis, encephalitis and fever.

In immunocompromised patients, especially in the case of AIDS, *T. gondii* causes a severe pathology. In approximately 30 percent of Toxoplasma-antibody positive patients with AIDS, toxoplasma encephalitis will develop due to reactivation of their latent infection. In immunocompetent humans, *T. gondii* infection induces a long-lasting protective immunity against reinfection (Remington & Krahenbühl, 1982) that could be attributed to the persistence of encysted parasites throughout the host life.

There are several strains of *T. gondii* known. One of the most important strains is the RH-strain which is highly virulent and originally isolated from human brain tissue.

Most investigations in the past regarding *T. gondii* were focused on the identification and molecular characterization of tachyzoite-specific antigens. More than 1000 different *T. gondii*-specific proteins have been identified. Surface proteins of *T. gondii* have been studied extensively. Of these surface-proteins the RH strain p30 surface protein is the most abundant; it constitutes approximately 5% of the total tachyzoite protein. The p30 surface protein is recognized intensively by human IgM, IgG, IgA and IgE antibodies (Decoster et al., Clin. Exp. Immunol., 73, 376–382, 1988; Godard et al., Infect. Immun., 58, 2446–2450, 1990) and is therefore useful for diagnostic purposes. Using monoclonal antibodies directed against p30, two immunocapture tests have been developed for the detection of anti-Toxoplasma IgM (Cesbron et al., J. Immunol. Methods, 83, 151–158, 1985) and IgA (Decoster et al., Lancet, ii, 1104–1106, 1988) antibodies.

The present invention provides new peptides, immunoreactive with antibodies to *T. gondii,* that can be used in diagnosing *T. gondii* infections in humans.

In particular the present invention provides peptides, immunoreactive with antibodies to *Toxoplasma gondii,* comprising part of the amino acid sequences as shown in SEQ ID No.: 1.

A preferred embodiment of the present invention are peptides comprising at least part of the amino acid sequences shown in SEQ ID No. 3 or 5.

Another preferred embodiment of the present invention are polypeptides comprising polymeric forms of said peptides.

SUMMARY OF THE INVENTION

The term "peptide" as used herein refers to a molecular chain of amino acids with a biological activity, and does not refer to a specific length of the product. Thus inter alia, proteins, oligopeptides, polypeptides and fusion-peptides as well as fusion-proteins are included.

The term "polypeptide" refers to dimeric, trimeric, . . . , polymeric forms of any length of a peptide according to the present invention.

The term "peptide" as used herein further refers to so-called functional variants, for example, acid addition salts, amides, esters, and specifically C-terminal esters, and N-acyl derivatives of the peptides according to the invention. These functional variants are considered to be part of the present invention. Also included are peptides which are modified in vivo or in vitro, for example by glycosylation, amidation, carboxylation or phosphorylation. It will be understood that for the particular proteins or polypeptides embraced herein, natural variations can also exist. These variations may be demonstrated by (an) amino acid difference(s) in the overall sequence or by deletions, substitutions, insertions, inversions or additions of (an) amino acid(s) in said sequence. Amino acid substitutions from which can be expected that they do not essentially alter biological and immunological activities, have been described. Amino acid replacements or conservative replacements between related amino acids or replacements which have occurred frequently in evolution are, inter alia Ser/Ala, Ser/Gly, Asp/Gly, Asp/Asn, Ile/Val (see Dayhof, M. D., Atla of protein sequences and structure, Nat. Biomed. Res. Found., Washington D.C., 1978, vol. 5, suppl. 3).

The term "part of the amino acid sequence" as used herein means an amino acid sequence comprising a subsequence of a peptide of the invention. Said parts or fragments are peptides comprising at least one antigenic determinant of the amino acid sequence as shown in SEQ ID No.: 1. Examples of these fragments are for instance peptides comprising the amino acid sequence as shown in SEQ ID No.: 3 or 5. Fragments can inter alia be produced by enzymatic cleavage of precursor molecules, using restriction endonucleases for the DNA and proteases for the polypeptides. Other methods include chemical synthesis of the fragments or the expression of peptide fragments by DNA fragments.

Suitable antigenic fragments of a peptide according to the invention containing (an) epitope(s) can be found by means of the method described in Patent Application WO 86/06487, (Geysen, H. M. et al. (Proc. Natl. Acad. Sci. 81, 3998–4002, 1984;, Geysen, H. M. et al. J. Immunol. Meth. 102, 259–274, 1987) based on the so-called pepscan method, wherein a series of partially overlapping peptides corresponding with partial sequences of the complete polypeptide under consideration, are synthesized and their reactivity with antibodies is investigated.

The minimal antigenic fragments of the epitopes can be found by synthesizing a series of partially overlapping peptides consisting of a gradually increase in amino acids per scan. The minimal immunoreactive core-structure of the epitope can be used to synthesize polymeric synthetic peptides on branched lysine molecules. Application of these branched peptides in a diagnostic assay results in an increase in immunoreactive sites for antibodies whereof the sensitivity of the assay can significantly be increased.

DETAILED DESCRIPTION OF THE INVENTION

The peptides comprising part of the amino acid sequence as shown in SEQ ID No.: 1 (representing clone #114) and preferred the peptides according to the present invention comprising the amino acid sequence as shown in SEQ ID No.: 3 or 5, are recognized by human anti-*T. gondii* antibodies of the IgG- as well as IgM-class respectively, and are therefore suitable diagnostic markers for *T. gondii* infections.

In SEQ ID No.: 1 the amino acid sequence are given for proteins with a (calculated) molecular weight of approximately 25.6 kD.

The preparation of the peptides or fragments thereof according to the invention is effected by means of one of the known organic chemical methods for peptide synthesis or with the aid of recombinant DNA techniques. This latter method involves the preparation of the desired peptide by means of bringing to expression a recombinant polynucleotide with a polynucleotide sequence which is coding for one or more of the peptides in question in a suitable micro-organism as host.

The organic chemical methods for peptide synthesis are considered to include the coupling of the required amino acids by means of condensation reaction, either in homogeneous phase or with the aid of a so-called solid phase.

The condensation reaction can be carried out as follows:

a) condensation of a compound (amino acid, peptide) with a free carboxyl group and protected other reactive groups with a compound (amino acid, peptide) with a free amino group and protected other reactive groups, in the presence of a condensation agent;

b) condensation of a compound (amino acid, peptide) with an activated carboxyl group and free or protected other reaction groups with a compound (amino acid, peptide) with a free amino group and free or protected other reactive groups.

Activation of the carboxyl group can take place, inter alia, by converting the carboxyl group to an acid halide, azide, anhydride, imidazolide or an activated ester, such as the N-hydroxy-succinimide, N-hydroxy-benzotriazole or p-nitrophenyl ester.

The most common methods for the above condensation reactions are: the carbodiimide method, the azide method, the mixed anhydride method and the method using activated esters, such as described in The Peptides, Analysis, Synthesis, Biology Vol. 1–3 (Ed. Gross, E. and Meienhofer, J.) 1979, 1980, 1981 (Academic Press, Inc.).

Preparation of suitable fragments of above-mentioned peptides according to the invention using the "solid Phase" is for instance described in J. Amer. Chem. Soc. 85, 2149 (1963) and Int. J. Peptide Protein Res. 35, 161–214 (1990).

As already indicated above, the peptides according to the invention can likewise be prepared with the aid of recombinant DNA techniques. For example, the peptides according to the invention can be incorporated in a repeating sequence ("in tandem") or can be prepared as a constituent of a (much larger) protein or polypeptide. This type of peptides therefore likewise falls within the scope of the invention.

For this purpose, as a constituent of a recombinant DNA, a nucleic acid sequence is used which codes for a peptide according to the invention and which, furthermore, is substantially free from nucleic acid segments, which in the naturally occurring *T. gondii* genome flank the nucleic acid sequence indicated above.

This latter method involves the preparation of the desired peptide by means of bringing to expression a recombinant polynucleotide with a nucleic acid sequence which is coding for one or more of the peptides in question in a suitable micro-organism as host.

The invention further encompasses nucleic acid sequences encoding the peptides according to the present invention and nucleic acid sequences comprising part of the nucleic acid sequence shown in SEQ ID No.: 2. Fragments of these nucleic acid sequences as shown in SEQ ID No.: 2 are for instance the nucleic acid sequences as shown in SEQ ID No.: 4 or 6. A further object of the present invention are nucleic acid sequences encoding peptides as shown in SEQ ID No.: 3 or 5.

The invention also comprises (a) host cell(s) transformed or transfected with a nucleic acid sequence or recombinant expression vector molecule, capable of producing the peptides according to the invention by expression of the corresponding nucleic acid sequence.

"Nucleic acid sequence" as used herein refers to a polymeric form of nucleotides of any length, both to ribonucleic acid sequences and to deoxy ribonucleic acid sequences. In principle, this term refers to the primary structure of the molecule. Thus, this term includes double and single stranded DNA, as well as double and single stranded RNA, and modifications thereof.

A nucleic acid sequence according to the present invention can be ligated to various replication effecting DNA sequences with which it is not associated or linked in nature resulting in a so called recombinant vector molecule which can be used for the transformation of or transfection into a suitable host. Useful recombinant vector molecules, are preferably derived from, for example plasmids, bacteriophages, cosmids or viruses.

Specific vectors or cloning vehicles which can be used to clone nucleic acid sequences according to the invention are known in the art and include inter alia plasmid vectors such as pBR322, the various pUC, pGEM and Bluescript plasmids, bacteriophages, e.g. lambda gt-Wes, Charon 28 and the M13 derived phages or viral vectors such as SV40, adenovirus, Semliki Forest Virus, vaccinia virus, Herpes viruses or polyoma virus (see also Rodriquez, R. L. and D. T. Denhardt, ed., Vectors: A survey of molecular cloning vectors and their uses, Butterworths, 1988; Lenstra, J. A. et al., Arch. Virol. 110, 1–24, 1990). The methods to be used for the construction of a recombinant vector molecule according to the invention are known to those of ordinarily skill in the art and are inter alia set forth in Maniatis, T. et al. (Molecular Cloning A Laboratory Manual. second edition; Cold Spring Harbor Laboratory, 1989).

For example, the insertion of the nucleic acid sequence according to the invention into a cloning vector can easily be achieved when both the genes and the desired cloning vehicle have been cut with or either one of them has been digested with the same restriction enzyme(s) as complementary DNA termini are thereby produced.

The recombinant vector molecules may additionally contain one or more marker activities that may be used to select for desired transformants, such as ampicillin and tetracycline resistance in pBR322, as for example ampicillin resistance and α-peptide of β-galactosidase in pUC8.

A suitable host cell is a micro-organism or cell which can be transformed by a nucleic acid sequence encoding a polypeptide or by recombinant vector molecule comprising such a nucleic acid sequence and which can if desired be used to express said polypeptide encoded by said nucleic acid sequence. The host cell can be of procaryotic origin, e.g. bacteria such as *Escherichia coli, Bacillus subtilis* and Pseudomonas species; or of eucaryotic origin such as yeasts, e.g. *Saccaromyces cerevisiae* or higher eucaryotic cells such as insect, plant or mammalian cells, including HeLa cells and Chinese hamster ovary (CHO) cells.

Information with respect to the cloning and expression of the nucleic acid sequence of the present invention in eucaryotic cloning systems can be found in Esser, K. et al. (Plasmids of Eucaryotes, Springer-Verlag, 1986).

In general, prokaryotes are preferred for the construction of the recombinant vector molecules useful in the invention. For expression nucleic acid sequences of the present invention are introduced into an expression vector, i.e. said sequences are operably linked to expression control sequences. Such control sequences may comprise promoters, enhancers, operators, inducers, ribosome binding sites etc. Therefore, the present invention provides a recombinant vector molecule comprising a nucleic acid sequence encoding the peptides identified above operably linked to expression control sequences, capable of expressing the DNA sequences contained therein in (a) transformed host cell(s).

It should, of course, be understood that the nucleotide sequences inserted at the selected site of the cloning vector may include only a fragment of the complete nucleic acid sequence encoding the peptides according to the invention as long as the transformed or transfected host will produce a polypeptide having at least one or more antigenic determinants.

In order to purify the expressed polypeptides produced as described above, host cells transformed with a recombinant vector according to the invention are cultured in an adequate volume and the polypeptides produced are isolated from such cells or from the medium if the protein is excreted. Polypeptides excreted into the medium can be isolated and purified by standard techniques, e.g. salt fractionation, centrifugation, ultrafiltration, chromatography, gel filtration or immunoaffinity chromatography, whereas intra cellular polypeptides can be isolated by first collecting said cells, disrupting the cells, for example by sonication or by other mechanically disruptive means such as French press followed by separation of the polypeptides from the other intracellular components and forming isolated polypeptides. Cell disruption could also be accomplished by chemical (e.g. EDTA or detergents such as Triton X114) or enzymatic means such as lysozyme digestion.

Antibodies, immunoreactive with a peptide according to the invention are also part of the present invention.

The peptides or fragments thereof prepared and described above are used to produce antibodies, both polyclonal and monoclonal. Monoclonal antibodies directed against peptides according to the invention are considered to be part of the present invention.

The preparation of cell lines producing monoclonal antibodies may occur by, for example, the Köhler and Milstein technique (Köhler and Milstein devised the techniques that resulted in the formation monoclonal antibody-producing hybridomas (G. Köhler and C. Milstein, 1975, Nature 256:495; 1976, Eur. J. Immunol. 6:511–519)), transformation technique of B-lymphocytes with a fusion partner being either a human or a mouse-human hybrid myeloma cell line, or a direct fusion of an EBV-tranformed B cell line with said myeloma cell lines.

An immunochemical reagent comprising one or more peptides or antibodies according to the invention is also part of the present invention.

The term "immunochemical reagent" according to the invention usually consists of one more peptides according to the invention or antibodies according to the invention and a suitable support or a labeling substance. Supports which can be used are, for example, the inner wall of a microtest well or a cuvette, a tube or capillary, a membrane, filter, test strip or the surface of a particle such as, for example, a latex particle, an aldehyde particle (such as a ceramic magnetizable particle with active aldehyde surface groups), an erythrocyte, a dye sol, a metal sol or metal compound as sol particle, a carrier protein such as BSA or KLH.

Labeling substances which can be used are, inter alia, a radioactive isotope, a fluorescent compound, an enzyme, a dye sol, a metal sol or metal compound as sol particle.

In a method for the detection of antibodies directed against *T. gondii* in a sample, an immunochemical reagent according to the invention is brought into contact with the sample. After which, the presence of immune complexes formed between the peptide and antibodies in the sample is detected and by this detection the presence of *T. gondii* antibodies in the sample is known and can be determined quantitatively.

Depending on the nature and further characteristics of the immunochemical reagent the immunochemical reaction that takes place is a so called sandwich reaction, an agglutination reaction, a competition reaction or an inhibition reaction.

For the detection of *T. gondii* in a sample an immunochemical reagent according to the invention, containing one or more peptides according to the invention, can be brought into contact with the sample and anti-*T. gondii* antibodies after which the presence of immune complexes formed can be detected and, from this, the presence of *T. gondii* in a sample can be determined.

A particularly suitable method for the detection of *T. gondii* in a sample is based on a competition reaction between a peptide according to the invention provided with a labeling substance and a *T. gondii* antigen (present in the sample) whereby the peptide and the antigen are competing with the antibody directed against *T. gondii* attached to a solid support.

An antibody according to the invention may also be brought into contact with a sample after which the presence of immune complexes formed is detected which is a measure for the presence of *T. gondii* in the sample.

A test kit according to the invention may comprise as an essential constituent an immunochemical reagent as described above. For carrying out a sandwich reaction, for the detection of *T. gondii* antibodies the test kit may comprise, for example, the peptide according to the invention coated directly or via a carrier-protein, i.e. BSA, to a solid support, for example the inner wall of a microtest well, and either a labeled peptide according to the invention or a labeled anti-antibody.

For carrying out a competition reaction, the test kit may comprise a peptide according to the invention coated to a solid support, and a labeled antibody directed against *T. gondii* preferably a monoclonal antibody directed against said peptide.

In an agglutination reaction the test kit comprises an immunochemical reagent which may comprise a peptide according to the invention coated to particles or sols. Another embodiment of a test kit is, for example, the use of a labeled peptide according to the invention as immunochemical reagent in a competition reaction with a *T. gondii* antigen to be detected for a binding site on the antibody directed against *T. gondii*, which is coated to a solid support.

It is within the scope of this invention to use the new nucleic acid sequences according to the invention as the basis of a test to detect *T. gondii* by a nucleic acid amplification technique for instance the polymerase chain reaction (PCR) or the nucleic acid sequence based amplification (NASBA), as described in EP 201,814 and EP 329,822, respectively. A method for the amplification and the detection of a *T. gondii* nucleic acid sequence in a sample using at least one nucleic acid sequence or fragment thereof according to the invention primer(s) in order to perform a nucleic acid amplification of said *T. gondii* nucleic acid sequence and to detect the amplified sequence is also part of the present invention. Part of the invention is also a test amplification technique, said kit containing at least a set of primers corresponding to at least a part of the nucleotide sequences according to the invention.

It is within the scope of this invention to use the new peptides or fragments thereof according to the invention as the basis of transport of co-expressed heterologous proteins to the surface of the plasma membrane of *T. gondii* or another parasitic organism or eucaryotic host cell via a phosphatidylinositol glycan (PI-G) moiety. A method for the intracellular transport and surface expression of a heterologous polypeptide or fragments thereof by using at least the hydrophobic $NH_2$-terminal signal peptide sequence that might be cleaved by an $NH_2$-terminal signal peptidase and the hydrophobic COOH-terminal peptide that in some way interacts with a putative transamidase that cleaves the peptide and concomitantly adds the PI-G-moiety. Part of the invention is also to use the $NH_2$-terminal signal peptide and COOH-terminal peptide sequences for the development of a heterologous expression cassettes in parasites and eucaryotic host cells.

Vaccines for the protection against *Toxoplasma gondii* are also part of the present invention. These vaccines comprise a host cell according to the invention or a peptide according to the invention or a polypeptide according to the invention, together with a pharmaceutical acceptable carrier.

The vaccine according to the invention can be administered in a conventional active immunization scheme: single or repeated administration in a manner compatible with the dosage formulation and in such amount as will be prophylactically effective, i.e. the amount of immunizing antigen or recombinant micro-organism capable of expressing said antigen that will induce immunity against challenge by virulent *Toxoplasma gondii* parasites. Immunity is defined as the induction of a significant level of protection in a population after vaccination compared to an unvaccinated group.

The administration of the vaccine can be done, e.g. intradermally, subcutaneously, intramuscularly, intraperitoneally, intra-venously, orally or intranasally.

Additionally the vaccine may also contain an aqueous medium or a water containing suspension, often mixed with other constituents, e.g. in order to increase the activity and/or shelf life. These constituents may be salts, pH buffers, stabilizers (such as skimmed milk or casein hydrolysate), emulsifiers, adjuvants to improve the immune response (e.g. oils, muramyl dipeptide, aluminiumhydroxide, saponin, polyanions and amphipatic substances) and preservatives.

The invention is further exemplified by the following examples:

EXAMPLE 1

Large Scale Preparation of *Toxoplasma gondii* Tachyzoites

The work described here uses the RH strain of *T. gondii* which is the most commonly used laboratory strain in Toxoplasma research. Large scale preparation of *T. gondii* tachyzoites was carried out by infecting cell factories (6000 cm$^2$) containing Vero cells with the tachyzoites at a multiplicity of infection of 0.30–1.0. After 3 days of culturing at 37° C., medium was removed and cells refed with the same medium. Six days after infection, culture supernatants were harvested and remaining Vero cells were washed with 200 ml PBS. Supernatants were pooled and tachyzoites were filtered on 10-μm polycarbonate membranes (Nucleopore, Pleasanton, Calif., USA) and washed twice with PBS. Tachyzoites were spin down (1,200 ×g, 5 min.) and stored at −70° C.

EXAMPLE 2

Construction of the Gene Library

Tachyzoite RNAs were isolated from 1.7×10$^9$ parasites as described previously. The total amount of isolated RNA (160 μg) was applied on an oligo(dT)-cellulose column (50 mg Pharmacia) yielding 6.5 μg polyadenylated RNA (Maniatis, 1982). cDNA synthesis was performed according to the method of Gubler and Hoffman (1983). Briefly, 2 μg poly (A)$^+$-RNA was denatured with 3 mM methylmercury hydroxide in 6 μl final volume during 5 minutes at ambient temperature (AT) (Lenstra et al., 1988). After neutralization by adding 1 μl of 280 mM β-mercaptoethanol to the reaction mix, first strand cDNA was synthesized in 25 μl reaction mix consisting of 0.5 μg oligo(dT) primer (Pharmacia, Uppsala, Sweden), 0.5 mM dNTPs, 2 mM DTT, 5 μl 5× RT-buffer (Gibco BRL), 10 μCi α-$^{32}$P dTTP, 10 μCi α-$^{32}$P dGTP (3000 Ci/mmol; Amersham, England) and 400 U M-MuLV reverse transcriptase (Gibco BRL). After 1 hour incubation at 37° C., second-strand synthesis was performed by adding 0.5 U RNase H (Pharmacia LKB, Uppsala, Sweden) and 10 U Klenow Polymerase I (Boehringer, Mannheim, Germany) to the first strand reaction mix. The reaction mix was incubated subsequently for 1 hour each at 11° C. and at 22° C. Five microgram *E. coli* tRNA (Boehringer, Mannheim, Germany) was added as carrier and the reaction mix volume was expanded to 100 μl with deionized water. The reaction mix was extracted with an equal volume phenol/chloroform (1:1), and subsequently with chloroform. Unincorporated dNTPs and small size cDNAs were removed by size fractionation on a Bio-Gel AcA34 column prepared in a 1 ml Pasteur pipette. The column was developed with TEN-buffer (10 mM Tris-HCl pH 7.4, 1 mM EDTA, 400 mM NaCl). The cDNA containing fractions were pooled (450 μl) and the cDNA strands were concentrated by ethanol precipitation using 5 μg *E. coli* tRNA as carrier. To prepare blunt-end cDNA strands, precipitated cDNAs were flushed in 75 μl reaction mix consisting of 67 mM Tris-HCl pH 8.8, 16.6 mM (NH$_4$)$_2$SO$_4$, 6.7 mM MgCl$_2$, 67 μM EDTA, 10 mM β-mercaptoethanol, 100 μM dNTPs and 8 Units T4-DNA-polymerase (Promega) and incubated during 10 minutes at 24° C. Subsequently, 4 Units Klenow Polymerase I (Boehringer, Mannheim, Germany) were added and incubation at 24° C. was continued for 10 min. The reaction mix was extracted with phenol and chloroform as described above. Unincorporated dNTPs and small size cDNAs were removed by size fractionation on a Bio-Gel AcA34 column as described above. Fractions containing the $^{32}$P-labelled cDNAs were pooled and concentrated by ethanol precipitation. For cloning into EcoRI-digested bacteriophage lambda gt11 vector, cDNA strands were tailed with G-residues and amplified by PCR using a poly-C-primer flanked by an EcoRI restriction site sequence at the 5'-end. Approximately 2.5% of the total cDNA sample was used for dG-tailing. The reaction mix (10 μl) consisted of terminal deoxynucleotidyl transferase (TdT)-buffer (Gibco BRL), 100 μM dGTP and 1 Unit TdT. After 30 minutes incubation at 37° C. the reaction mix was extracted with phenol and chloroform, ethanol precipitated and the pelleted DNA was dissolved in 10 μl H$_2$O. Amplification with the poly-C primer was performed by applying 1 μl of different concentrations (undiluted, 10$^2$, 10$^4$ and 10$^6$-fold dilutions) of the cDNA sample in amplification mix. The final volume of the amplification mix was 50 μl and consisted of Taq-buffer (Cetus.) 200 μM dNTPs and 500 ng of primer. Following 40 cycles of amplification (1 minute (min.) at 94° C., 5 minutes at 55° C., 3 minutes at 68° C.), 5 μl of each sample was analyzed on a 1.5% agarose gel (Tris-acetate buffered).

In order to determine the efficiency of amplifying Toxoplasma specific sequences, DNA fragments were separated and blotted onto nitrocellulose filter and hybridized with a nick-translated Toxoplasma-specific 1 kb probe encoding the p30 polypeptide (Burg et al., 1988). The PCR sample obtained with the 100-fold diluted cDNA template yielded the strongest hybridization signal. The physical lenght of the amplified cDNA fragments in this sample varied between 300–500 base pairs. Therefore, this sample was further processed in the cloning studies. The sample mix was extracted and concentrated by ethanol precipitation as described above. In a reaction mix volume of 20 μl, DNA fragments were digested with 40 Units EcoRI restriction enzym during 6 to 8 hours at 37° C. Size selection of DNA fragments was performed as described above using a 5 ml AcA34 column. Fragments were concentrated by ethanol precipitation, and the pellet comprising cDNA molecules (300–500 bp) was dissolved in 10 μl sterile distilled water. The DNA sample (3 μl) was ligated to 0.5 μg EcoRI arms of lambda gt11 (Promega Corp., Madison, Wis.). The ligation reaction mix (5 μl) consisting of ligase buffer (Promega) and 4 U ligase (Promega) was incubated during 8 hours at 16° C.

In vitro packaging reactions were carried out according to standard procedures (Huynh et al., 1985). Briefly, 2.5 μl of the ligation mix was added to 25 μl packaging extract (Gigapack plus, Stratagene Cloning Systems) and incubated during 2 hours at 16° C. Subsequently, 250 μl SM-buffer (Maniatis, 1982) and 5 μl chloroform were added to the reaction mix. Following centrifugation, the supernatant was plaque titrated on *E. coli* Y1090 cells. The titer of the bacteriophage lambda gt11 library was 1.5×10$^6$ plaque forming units (p.f.u.). At least 98% of the phages was recombinant. To evaluate the library, *E. coli* Y1090 cells were infected with the recombinant phages (2×10$^3$ p.f.u.) and plated with LB-agar medium. Phage plaques thus formed were replicated onto nitrocellulose filters and were hybridized with a $^{32}$P nick-translated 1 kb fragment encoding for the p30 protein of *T. gondii* (Burg et al., 1988). Two positive reacting plaques were identified. Phages were isolated and inserts were amplified by PCR using lambda gt11 specific-forward and reverse primers. The forward and reverse primers comprised a BamHI and a HindIII restriction site at their 5'-end, respectively. BamHI- and HindIII-digested DNA fragments were isolated from an agarose gel by using the "freeze squeeze" method (Tautz and Renz, 1983) and cloned into BamHI/HindIII digested pMLB1113 (Organon Teknika Corporate, Durham, N.C.) and pGEM 4Z vectors (Promega). Sequence analysis of the cloned PCR fragments revealed that both inserts represented the carboxyl terminal sequence of the P30 gene.

EXAMPLE 3

Purification of Polyclonal Anti-Toxoplasma Antibodies

To find immunodominant antigens reactive with antibodies collected from patients acutely infected with *T. gondii*, sera were collected from five *T. gondii* infected human adults, were pooled and the IgG and IgM fractions were separated and fractionated by affinity chromatography using Protein G Sepharose 4 Fast Flow (LKB Pharmacia, Uppsala, Sweden). The flow-through fraction (sample A) containing IgM antibodies was used to screen the cDNA library. The absorbed antibodies (sample B), i.e. IgG, were eluted and stored at −20° C. The purity of both sample A and sample B was evaluated in an IgM and IgG specific ELISA.

EXAMPLE 4

Immunoscreening of the *T. gondii* Library

*E. coli* Y1090 was cultured overnight using LB medium (Maniatis, 1982) which had been supplemented with 50 μg/ml of ampicillin and 2 g/l maltose. A 0.5 ml portion of the cultured broth was mixed with 0.5 ml SM-buffer and 10 μl of the recombinant phage ($5 \times 10^4$ pfu) which had been prepared according to Example 2. The cell suspension was incubated at 37° C. for 15 minutes in order to complete transfection. The cell suspension was mixed with 10 ml of LB medium supplemented with 0.70% agarose (Seahem) and 100 μg/ml ampicillin (Boehringer, Mannheim, Germany) and the mixture was poured on a plate containing LB-agar medium. After incubating the plate at 42° C. for 4 hours, nitrocellulose filters soaked with 10 mM isopropyl β-D-thiogalactopyranoside (IPTG; Boehringer, Mannheim, Germany) were put on the overlay agar medium and the plate was incubated again at 42° C. for 2 hours. Phage plaques thus formed were replicated onto the filters. Duplicate filters were prepared from the same plate.

Binding sites on the filters were blocked by incubating the filters either for 1 hr at ambient temperature or overnight at 4° C. with TBS solution supplemented with 20% fetal calf serum (FCS). The replica filters were incubated at room temperature for 2 hours in TBST solution (Promega Corp., Madison, Wis.) containing 1/250 diluted sample A (Example 3). The filters were washed three times (5 minutes for each) at room temperature with 100 mM phosphate buffer (pH 7.2) containing 0.05% Tween 20 in order to remove unreacted antibody. Subsequently, the washed filters were incubated at room temperature for 2 hours with 1/2000 diluted alkaline phophatase conjugated mouse anti-human IgM monoclonal antibodies (Zymed Lab., San Francisco, Calif.). The filters were washed three times (5 minutes for each) at room temperature as described above. Positive clones were identified by adding BCIP/NBT (Promega Corp., Madison, Wis.) as a substrate. More than 20 positive plaques were identified based on the colouring reaction. Six positive plaques i.e. No. 101, 105, 106, 107, 112, and 114, were random chosen and plaque-purified.

EXAMPLE 5

Screening of Positive Clones

Thirteen positive clones were isolated after the single plaque purification round and were designated No. 10A, 101B, 105, 106, 107A, 107B, 107C, 107D, 112A, 112B, 114A, 114B, 114C. Crude lysates containing the 13 recombinant antigens were prepared by lytic growth of the six lambda gt11 recombinants in *E. coli* Y1090. Briefly, Y1090 cells were grown to saturation in LB-medium (pH 7.5) supplemented with ampicillin (100 μg/ml), glucose (0.2%) and $MgSO_4$ (10 mM). An Y1090 cell suspension (10 μl saturated culture diluted in 1 ml SM-buffer) was infected with the lambda gt11 recombinant phages at a multiplicity of infection of approximately 0.1 for 15 minutes at room temperature. Infected cells were grown overnight at 37° C. in 5 ml LB medium supplemented with 100 μg/ml ampicillin. These saturated cell cultures were used to start 2 ml cultures in LB-medium supplemented with ampicillin. After 3–4 hours of culturing at 30° C., 1 mM IPTG was added and incubation was continued for another 3–4 hours at 30° C. Lysis was observed in some of these cell cultures. After centrifugation of 1 ml cell culture suspension, pelleted or cell debris were resuspended in 0.1 ml Laemmli sample buffer (Laemmli, 1970; Nature 227, 680–685). Protein samples were boiled for 5 minutes and 5 μl sample was analyzed by sodium dodecyl sulfate polyacrylamide gel electrophoresis (SDS-PAGE) and blotted onto nitrocellulose filters. Following ponceau-S staining, relative low amounts of cellular proteins were visible as compared to the β-galactosidase fusion protein. Triplicate blotstrips prepared of the six lambda gt11 recombinant lysogen lysates were incubated for 2 hours at room temperature either with mouse anti-β-galactosidase monoclonal antibody (filter nr 1.) and sample A (Example 3; filters nr 2 and 3) according to the conditions described in Example 4. Following washing, filter nr 1 was incubated with alkaline phosphatase conjugated goat anti-mouse antibodies (Promega Corp., Madison, Wis.). Filters nr 2 and 3 were incubated with alkaline phosphatase conjugated mouse anti-human IgM and alkaline phosphatase conjugated goat anti-human IgG (Promega Corp., Madison, Wis.), respectively. After incubation for 1 hour at room temperature, filters were washed and developed by adding BCIP/NBT as substrate (Promega Corp., Madison, Wis.). As shown in FIG. 1A, five out of six recombinant phages (i.e. No. 101, 105, 106, 112, 114) expressed a fusion protein larger in size than β-galactosidase. These fusion proteins also reacted with antibodies of the human anti-Toxoplasma IgM pool (FIG. 1B), whereas only clone #114 also reacted strongly with antibodies of the human anti-Toxoplasma IgG pool (FIG. 1C). All selected clones gave upon amplification with the lambda gt11 specific-forward and reverse primers a PCR fragment of approximately 350 bp. The fusion product of clone #114 was approximately 10 kDa larger in size than β-galactosidase. Clone #114 contained a large open reading frame (ORF). The PCR products were incubated with the BamHI and HindIII restriction enzymes and subcloned into pMLB1113 (Organon Teknika Corporate, Durham, N.C.) and pGEM 4Z vectors (Promega Corp., Madison, Wis.) as described above. Nucleotide sequences of the cloned inserts were determined by the dideoxy chain termination method using a T7-sequencing kit (Pharmacia LKB, Uppsala, Sweden). Sequence comparisons revealed that the nucleotide sequence of one out of six cloned inserts was similar to the nucleotide sequence of clone #114.

EXAMPLE 6

Determination of the Origin and Specificity of Clone #114

Northern and Southern blot experiments were performed in order to confirm that the isolated DNA fragments of clone #114 represented *T. gondii* encoded genes. Northern blot experiments: Poly(A)⁺ RNA of tachyzoites (Example 2) and total RNA extracted from mock-infected Vero cells, was denatured with glyoxal and dimethyl sulfoxide (DMSO) (McMaster and Carmichael, 1977 PNAS 74, 4835–4838), and analyzed by electrophoresis on a 1% agarose gel in 10 mM phosphate buffer pH 7.0. The gel was stained during 30 minutes in 50 mM NaOH supplemented with 10 μg/ml EtBr and destained during 30 minutes in 0.5M Tris 7.5 (FIG. 2A). Separated RNA species were blotted from the gel to nitrocellulose filters (20×SSC; Maniatis, 1982). Prehybridization was allowed to occur in 50% formamide, 6× SSPE (1× SSPE is 148.5 mM sodium chloride, 10 mM NaH$_2$PO$_4$, 1 mM EDTA pH 7.4), 10× Denhardt's (1× Denhardt's is 0.02% Ficoll, 0.02% polyvinylpyrrolidone, 0.02% bovine serum albumin), 100 μg/ml sonicated salmon sperm DNA and 0.1% SDS for 2 hours at 42° C. Hybridization at 42° C. for 16 hours was carried out with gel purified PCR-fragments of clone #114 and of the p30-probe (Example 2) radiolabeled with α-$^{32}$P by nick translation (FIG. 2B; Maniatis, 1982). After ethidium bromide staining, a considerable difference in electrophoretic mobility was observed between the ribosomal RNA species of T. gondii and Vero cells (FIG. 2A). Vero cell specific-ribosomal RNAs were not present in the toxoplasma RNA sample. Northern blot analysis of the poly(A)$^+$ selected RNA sample revealed that the full lenght mRNA species of clone #114 was 1500 nt. None of the probes hybridized to RNAs derived from uninfected Vero cells. The poly(A$^-$) fraction (void) was not completely depleted of poly(A$^+$) RNAs (FIG. 2B, lanes 2 and 3).

Both genomic and mitochondrial DNA isolated from purified tachyzoites (Example 1) and from uninfected Vero cells were digested with the restriction enzymes EcoRI and BamHI and subjected to Southern blot analysis. A radiolabeled probe prepared of clone #114 hybridized to EcoRI and BamHI digested DNA fragments of 9 and 7 kb, respectively. The probe did not hybridize to genomic DNA isolated from mock-infected Vero cells (FIG. 3).

Expressed recombinant fusion protein of clone #114 was evaluated by Western blot analysis using two serum panels of toxoplasma infected patients. A preparative SDS-PAGE was loaded with recombinant fusion protein of clone #114 (lytic grown) and a crude tachyzoite lysate resuspended in Laemmli sample buffer. Following transfer of the protein bands to nitrocellulose filters, strips were prepared and incubated during 16 hours at room temperature with 8 anti-Toxoplasma IgM$^+$/IgG$^+$ serum samples and with 8 anti-Toxoplasma IgM$^-$/IgG$^+$ serum samples (diluted 1/200). Strips were washed and incubated during 3 hours either with alkaline phosphatase conjugated goat anti-human IgM (dilution 1:2000) or with alkaline phosphatase conjugated goat anti-human IgG (diluted 1:5000). As a result, 4 out of 8 IgM$^+$-sera reacted strongly with the recombinant β-galactosidase fusion protein whereas the remaining four sera reacted only weakly (FIG. 4A). None of the IgM-serum samples recognized the recombinant fusion protein. These sera also did not immunoreact with the crude tachyzoite proteins (FIG. 4B) indicating that the alkaline phosphatase conjugated goat anti-human IgM does not crossreacts with human IgG antibodies. The IgM$^+$ sera reacted predominantly with tachyzoite-specific polypeptides with Mr of 30- and 38-kD.

Except for serum nr. 2, all serum samples tested revealed a very strong IgG specific immune response against the β-galactosidase fusion protein of clone #114 (FIG. 5). Among a number of tachyzoite specific polypeptides, again the 30- and 38-kD proteins were predominantly recognized by the tested serum samples.

EXAMPLE 7

Affinity Purification of Recombinant Antigen-specific Antibodies

Antibodies specific for recombinant antigen clone #114 were isolated from anti-T. gondii human immune IgG by affinity chromatography on nitrocellulose blotted recombinant antigen. These monospecific antibodies were used to detect the corresponding native T. gondii antigen on Western blot strips. Briefly, 0.5 ml cell suspension of a lytic grown phage was pelleted, analyzed on a preparative 12% SDS-PAGE and electrotransferred to a nitrocellulose filter. The recombinant fusion protein was localized by ponceau-S staining and an horizontal strip containing this protein was excised from the nitrocellulose sheet. After blocking and washing with Phosphate-buffered Saline Tween® (PBST), the membrane was incubated with anti-T. gondii human serum sample A (Example 3; diluted 1/10). Vertical 5 mm-wide strips were cut on one edge of the nitrocellulose sheet and incubated subsequentially with labelled second antibody and the chromogenic substrate in order to confirm the location of the reactive recombinant fusion protein. Monospecific antibodies were eluted from the strip by using 0.1M glycine-HCl pH 2.7 during 5 minutes at room temperature. The eluate was neutralized immediately by adding a pretitrated volume of 4M NaOH. Glycine treatment of the nitrocellulose strip was repeated and both neutralized fractions were pooled. Nitrocellulose strips containing total tachyzoite lysate were incubated overnight with the recombinant antigen-specific antibodies (diluted 1/10). Strips were incubated either with alkaline phosphatase conjugated mouse anti-human IgM or with IgG antibodies. A protein with a molecular weight of approximately 38 kD was detected in the strip developed with anti-human IgG (FIG. 6).

EXAMPLE 8

Complete DNA Sequences of Clone #114 and Deduced Amino Acid Sequences

The inserts of clone #114 were extended in both 3' and 5' direction in order to determine the entire nucleotide sequence of the gene. The 3'-end of the gene was cloned by cDNA synthesis using PCR. cDNA synthesis was primed with an oligo(dT)-XbaI primer. The reaction-mix consisting of 100 ng poly(A)$^+$ RNA, 500 ng oligo(dT)-XbaI primer and 5 mM (CH$_3$HgOH) methylmercuric hydroxide was incubated for 10 minutes at room temperature (Example 2). After neutralization with β-mercaptoethanol 200 mM DTT, 10 mM dNTP's, 25 U RNAse inhibitor (Pharmacia) and 200 U MMLV-RT (GIBCO BRL, Breda, The Netherlands) were added and incubation was continued for 30 minutes at 37° C. Subsequently, 15% of the cDNA mix was amplified by PCR. A internal primer localized on the 5'-end of clone #114 and extended with a BamHI restriction site functioned as second primer (Primer 666 for clone #114).

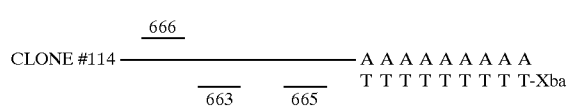

The physical lenght of the 3'-end amplified DNA fragments of clone #114 were 1250 bp. The 3'-end PCR fragments were digested with XbaI and BamHI restriction enzymes and purified on a 1.5% agarose gel using the Geneclean method. Digested DNA (70 ng) was cloned into the XbaI/BamHI digested pGem 7 vector (25 ng; Promega Corp., Madison, Wis.). Transformants were selected by PCR using the nested primer 663 for clone #114 in combination with the M13 reverse primer. Selected clones were sequenced.

The 5'-ends of the clone #114 gene were cloned by cDNA synthesis using 100 ng poly(A)$^+$ selected RNA. Primer 665 represented the 3'-ends of clone #114 and were used as primer. The cDNA fragments were size selected on a Bio-Gel AcA34 column (IBF Biotechnics). DNA fragments of ≧200 bp were tailed with dGTP using 15 U TdT (GIBCO BRL, Breda, The Netherlands). The tailed DNA fragments were amplified by PCR using the 3'-end primer 665 (flanked by a HindIII restriction enzyme site) and an oligo(dC)-EcoRI primer. Amplified fragments were digested with the HindIII and EcoRI restriction enzymes and separated on a 2% agarose gel. Amplified fragments were purified from the gel by the Gene-Clean method and cloned into an EcoRI/HindIII digested pUC18 vector. Transformants of clone #114 were screened by nested PCR using the M13 reverse primer and primer 663. Clones containing long inserts were subjected to sequence analysis using the T7 sequence analysis kit (Pharmacia). The physical length of the 5'-end extended fragments was 635 bp for clone #114. Comparing both 3'- and 5'-end extended sequences of clone #114, open reading frames of 690 bp were found (FIG. 7). The polypeptides encoded by the ORF of #114 have a calculated mass of 25.6 kD (SEQ ID No.: 1). The predicted polypeptide encoded by clone #114 was analyzed in more detail. The first ATG codon is found at position 199 and is surrounded by sequences fulfilling the criteria for initiation of translation (Kozak, 1986). In FIG. 8 the complete amino acid sequence of clone #114 (including a leader sequence) is shown. Furthermore, one potential N-linked glycosylation site is located at aa position 89 (FIG. 8) or 74 (SEQ ID No.: 1). The carboxyl-terminal end of polypeptide #114 comprises a hydrophobic domain indicative for a signal peptide sequence. Upstream of the hydrophobic domain several potential transamidase cleavage sites (GXG or GXA) are located.

The full lenght genes of clone #114 were cloned by PCR amplification using poly(A+) RNA and chromosomal DNA isolated from tachyzoites. The selected primers comprised both the 17 nucleotides upstream from the first predicted startcodon as well as an NcoI and EcoRI restriction enzym site. The 3'-end primers comprised both the last 17 nucleotides upstream from the predicted stopcodons as well as a SalI and BglII restriction enzym site. The physical lenght of the PCR fragments derived from both RNA and DNA was similar indicating that the genes did not contain introns. The amplified genes were cloned as β-galactosidase fusion constructs into an EcoRI/SalI digested pMLB 1113 vector. Upon transformation and selection (Maniatis, 1982), expressed recombinant fusion proteins were analyzed by SDS-PAGE and Western blot. Filters were incubated with a mouse monoclonal anti-β galactosidase antibody, Sample A, Sample B (Example 3) and normal human serum. The gene was also cloned into the NcoI/BglII sites of the pKK 233 vector and was expressed as non-fusion protein.

EXAMPLE 9

Mapping of Epitopes with Synthetic Peptides (PEPSCAN)

Overlapping 12-peptides covering the entire coding region of gene #114 (including the leader sequence) were synthesized and tested as previously described (Geysen et al., 1984, 1985). All peptides were tested against human anti-Toxoplasma IgM+ and IgG+ serum samples (diluted 1:100) in ELISA for extinction at 450 nm. The IgM+ antibodies tested did not recognize any of the synthetic peptides. The results obtained with IgG+ antibodies of Toxoplasma-infected individuals of p25,6 (encoding clone #114) are shown in FIG. 9. An immunodominant region at amino acid position 104–117 could be demonstrated. A synthetic peptide (SEQ ID No.: 3) comprising amino acid position 104–128 (25 aa) was synthesized and evaluated in ELISA (Example 10). The critical lenght of the immunodominant epitope was determined by PEPSCAN using overlapping 3-, 4-, 5-, 6-, 7-, 8-, 9-, 10-, 11-peptides (FIG. 10 and 11). The core structure of the epitope is defined by the amino acids Asp-Val-Asp-Pro-Phe-Pro (DVDPFP) (SEQ ID No.: 5) which fulfills the criteria for a β-turn.

EXAMPLE 10

Clinical Relevance of the Immunodominant Epitope of Clone #114

The synthetic peptide (SEQ ID No.: 3) comprising the amino acid sequence (AA position 104–128) was synthesized and coupled to bovine serum albumin (BSA). Microtiter plates were coated overnight at room temperature with 1.0 μg synthetic peptide in coating-buffer (carbonate-buffer, pH 9.6). After removal of the unbound antigen, plates were post-coated. After drying, the plates were stored at 4° C. until use. Panels of serum samples of Toxoplasma infected and uninfected patients were diluted (1:100) and added to the coated wells. Following 1 hour incubation at room temperature, wells were washed with PBST-solution and incubated with 100 μl horseradish peroxidase conjugated goat anti-human IgG. After one hour incubation at 37° C., wells were washed with PBST and the antigen-antibody complexes were detected by the addition of TMB as substrate. After 30 minutes incubation the reaction was stopped by adding 100 μl 1M $H_2SO_4$ to the wells. Optical densities were measured at 450 nm. Cut-off value (COV) was calculated as the average of seronegative samples plus three times the standard deviation. As shown in FIG. 12 typically 12 out of 13 Toxoplasma antibody containing samples reacted with the peptide-BSA complex. None of the negative samples tested were significantly above the COV.

DESCRIPTION OF THE FIGURES

FIG. 1: SDS-PAGE pattern of protein samples blotted onto nitrocellulose filters.

FIG. 2: Determination of the origin and specificity of clone #114

FIG. 7: Open reading frame of clone #114.

FIG. 8: Amino acid sequence encoding clone #114

Figure 1A:
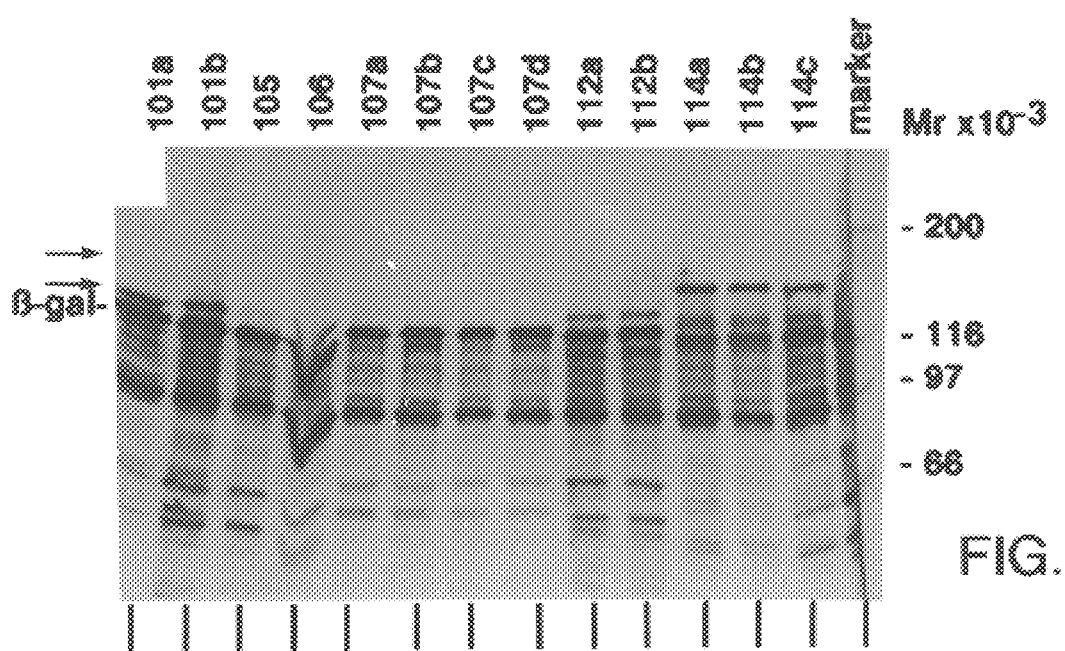
FIG. 1A: Filter nr 1 incubated with alkaline phosphatase conjugated goat anti-mouse antibodies.
Figure 1B:
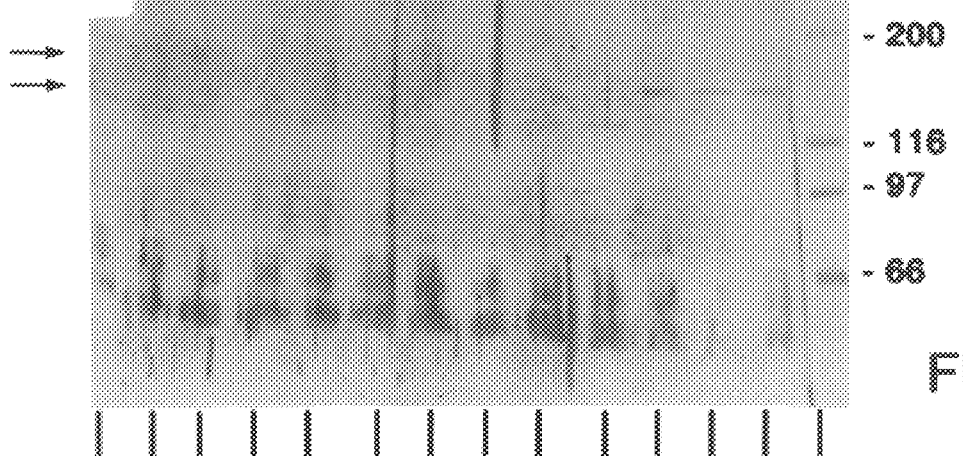
FIG. 1B: Filter nr 2 incubated with alkaline phosphatase conjugated mouse anti-human IgM.
Figure 1C:
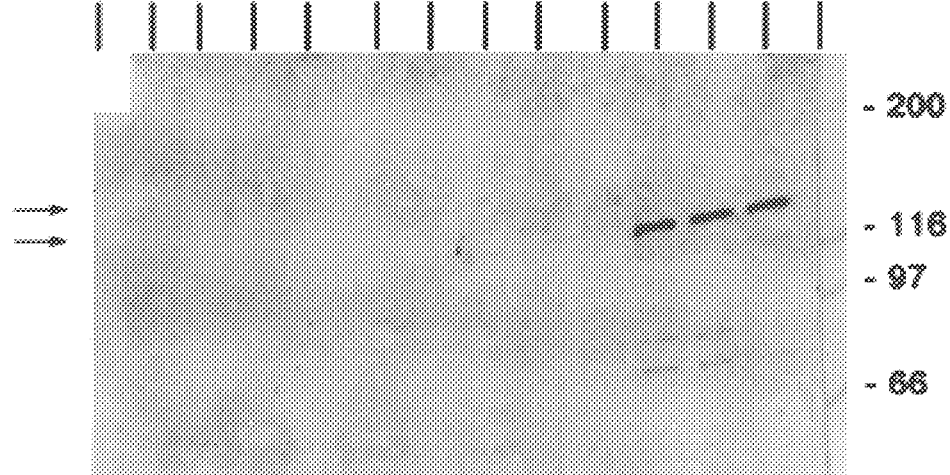
FIG. 1C: Filter nr 3 incubated with alkaline phosphatase conjugated goat anti-human IgG.
Figure 2A:
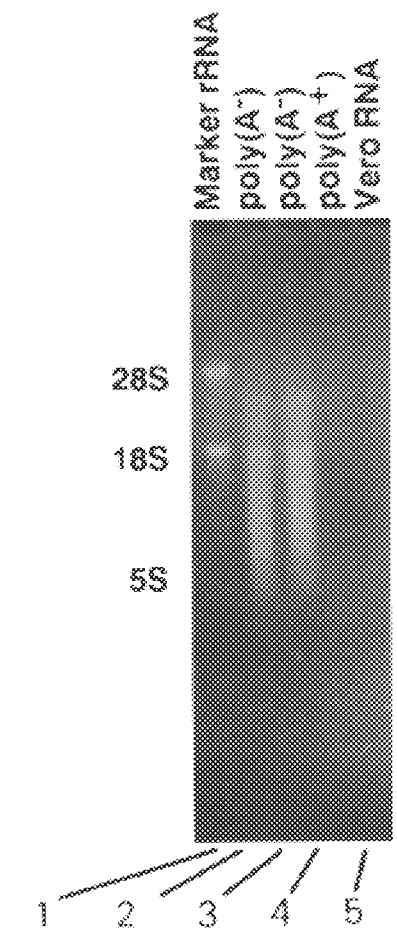
FIG. 2A: Analysis of electrophoretic mobility between the ribosomal RNA species of T. gondii and Vero cells.
Figure 2B:
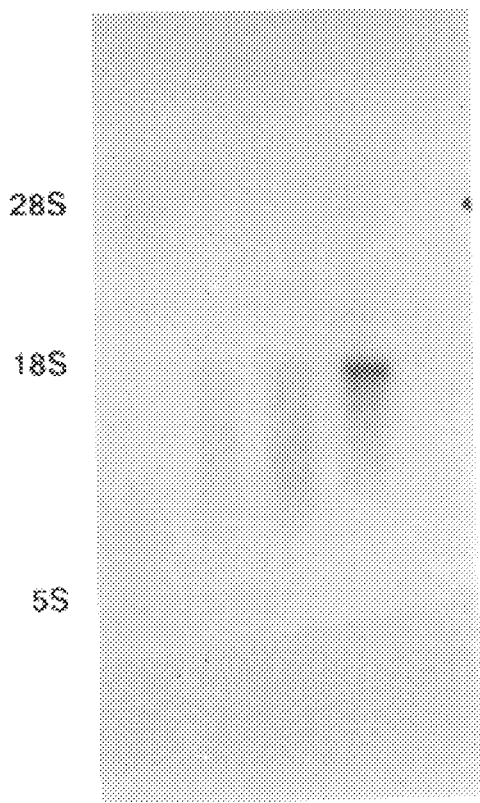
FIG. 2B: Northern blot analysis of the RNA of tachyzoites and total RNA extracted from mock-infected Vero cells. The full lenght mRNA species of clone #114 is 1500 nt.
Figure 3:
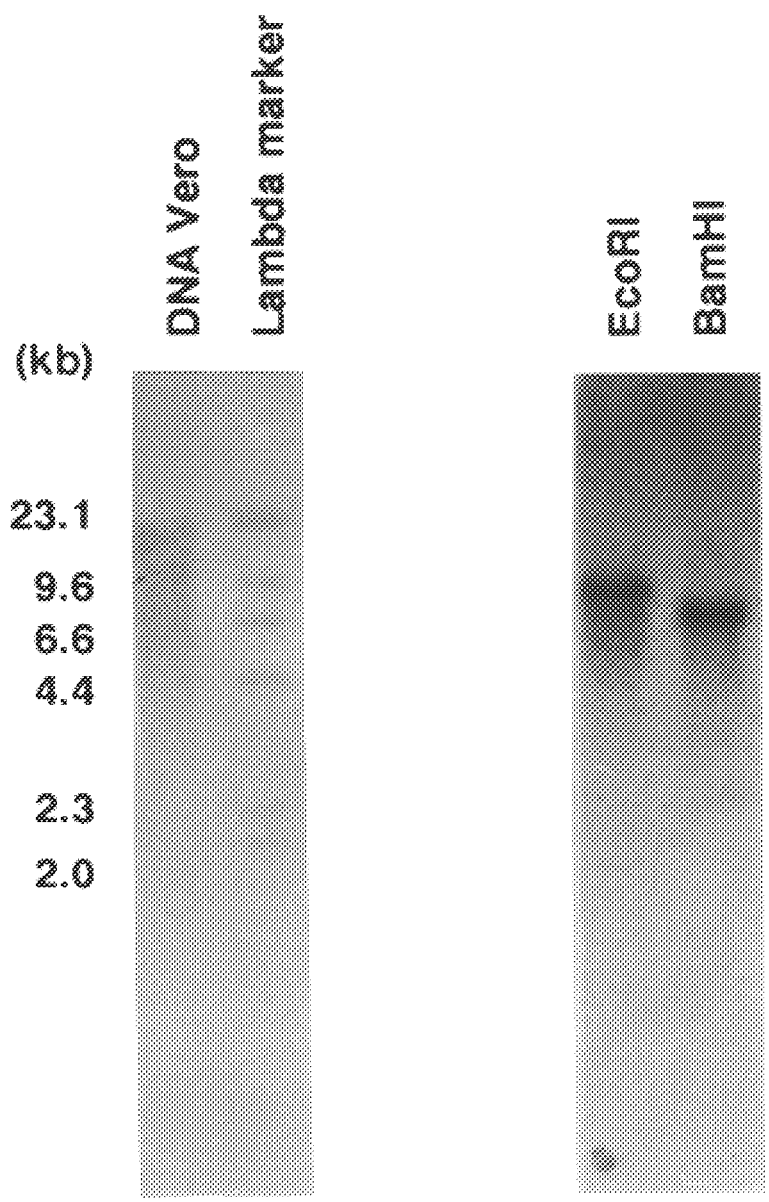
FIG. 3: Southern blot analysis of both genomic and mitochondrial DNA isolated from purified tachyzoites (Example 1) and from uninfected Vero cells.
Figure 4A:
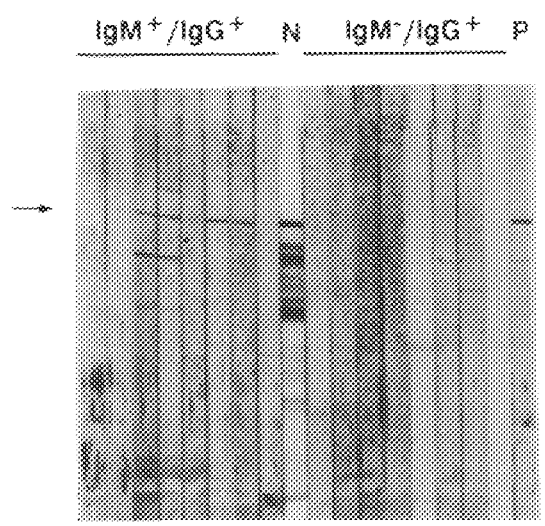
FIGS. 4+5: Western blot analysis of expressed recombinant fusion protein of clone #114 using two serum panels of Toxoplasma infected patients.
Figure 4B:
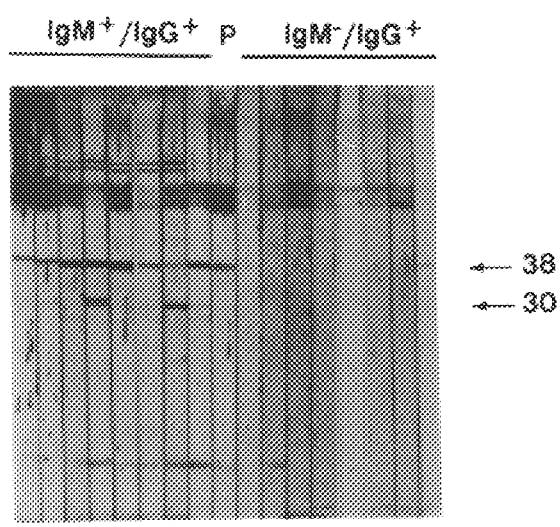
Figures 5A, 5B:
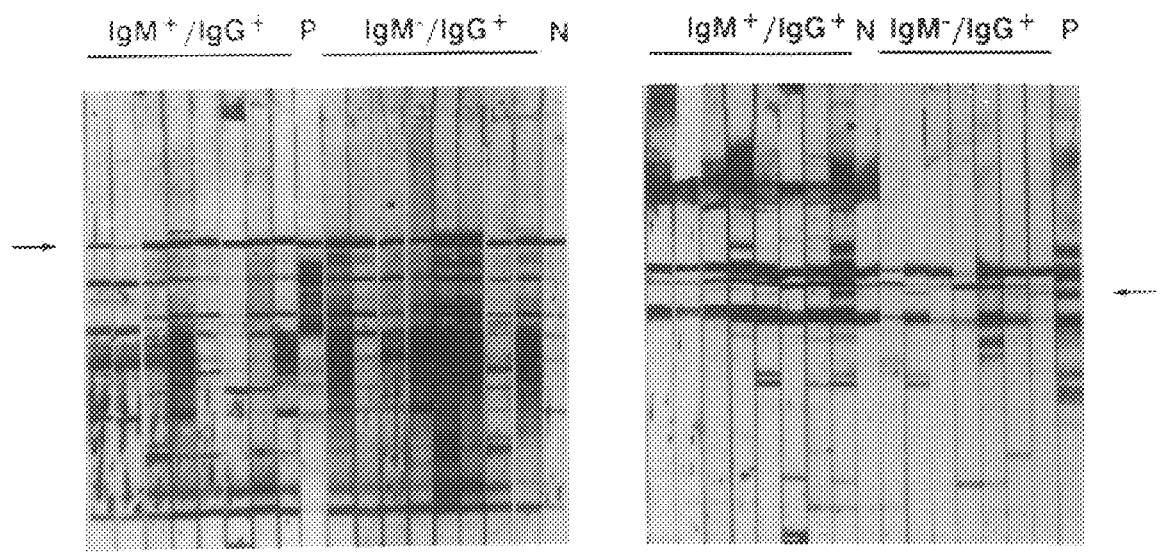
Figure 6:
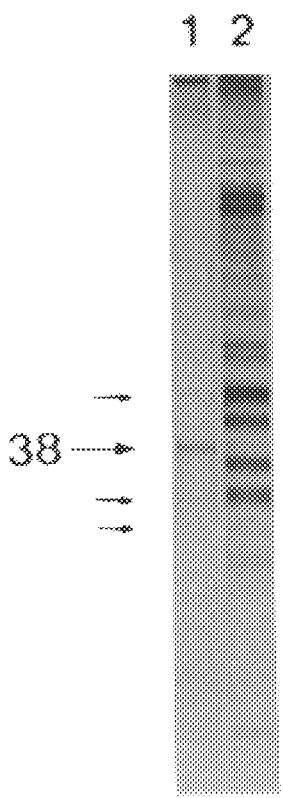
FIG. 6: Detection of native *T. gondii* antigens by affinity purified monospecific antibodies on Western blot strips.
Figure 9:
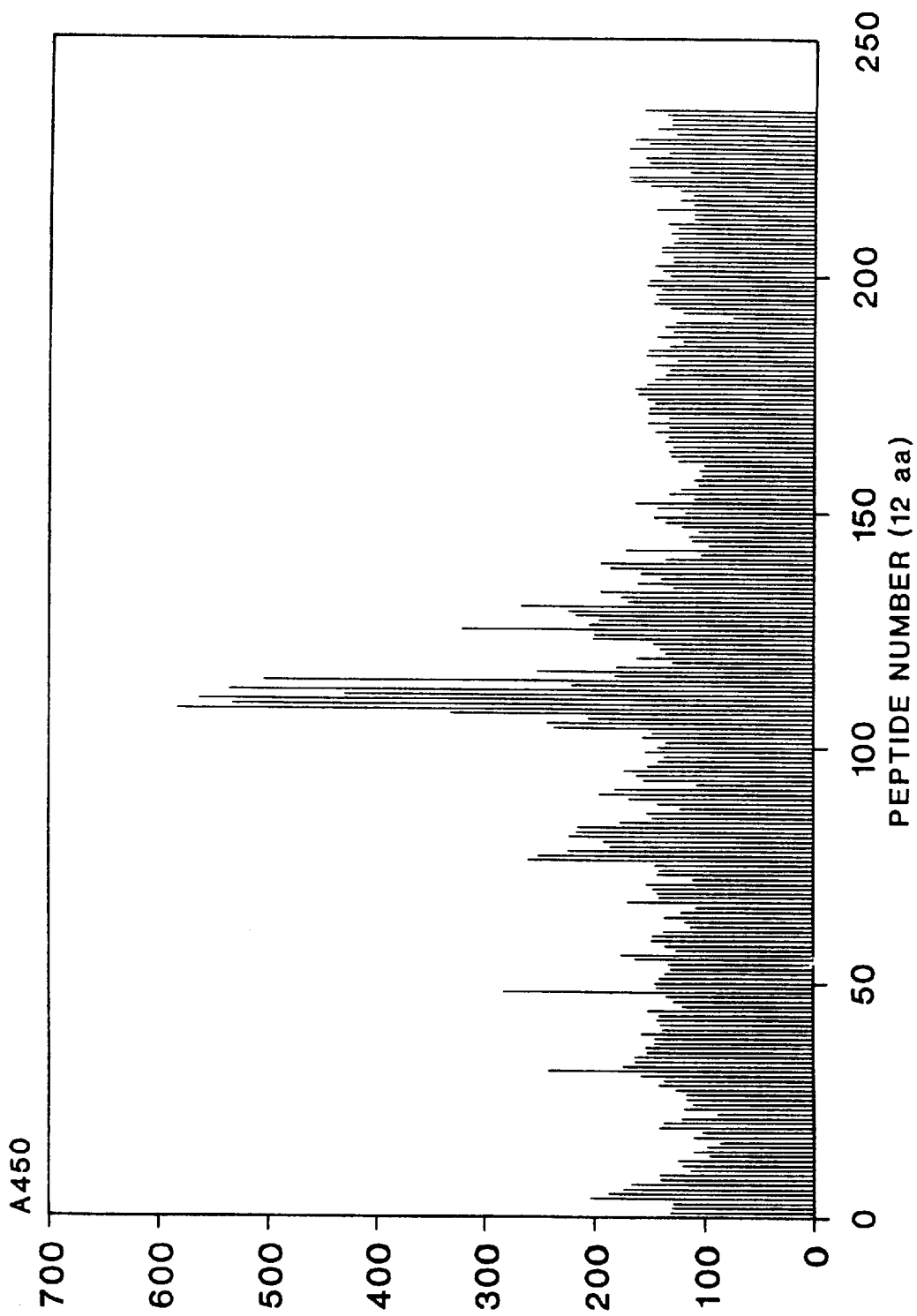
FIG. 9: Mapping of epitopes with synthetic peptides (PEPSCAN).
Figure 10A:
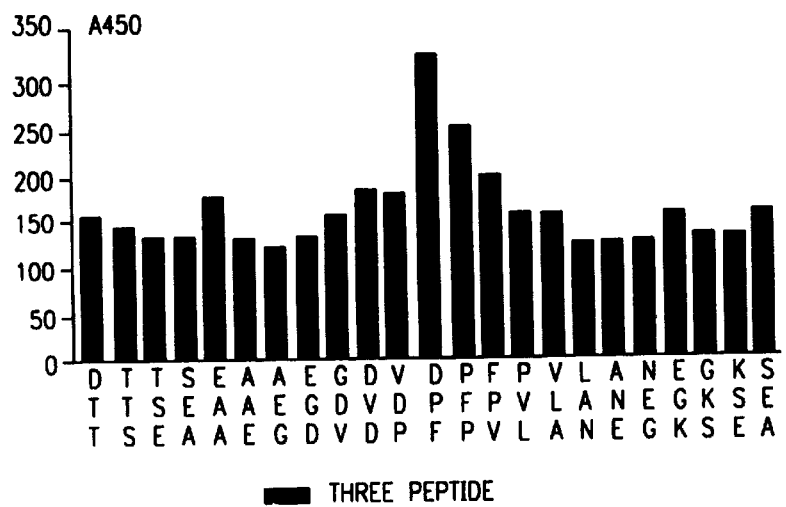
FIGS. 10+11: Determination of the critical length of an immunodominant epitope with synthetic peptides (PEPSCAN).
Figure 10B:
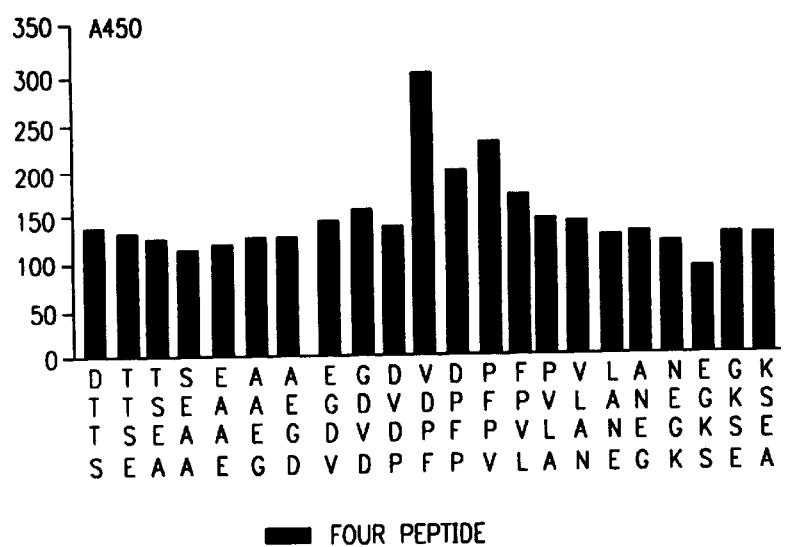
Figure 10C:
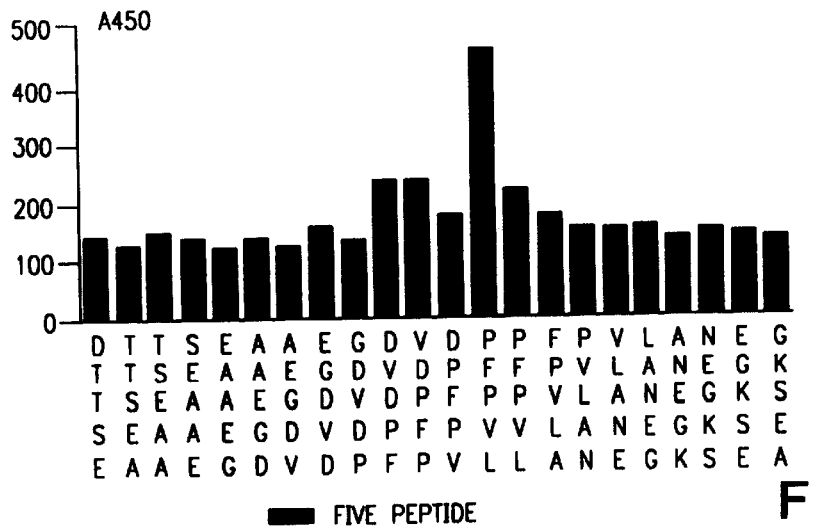
Figure 10D:
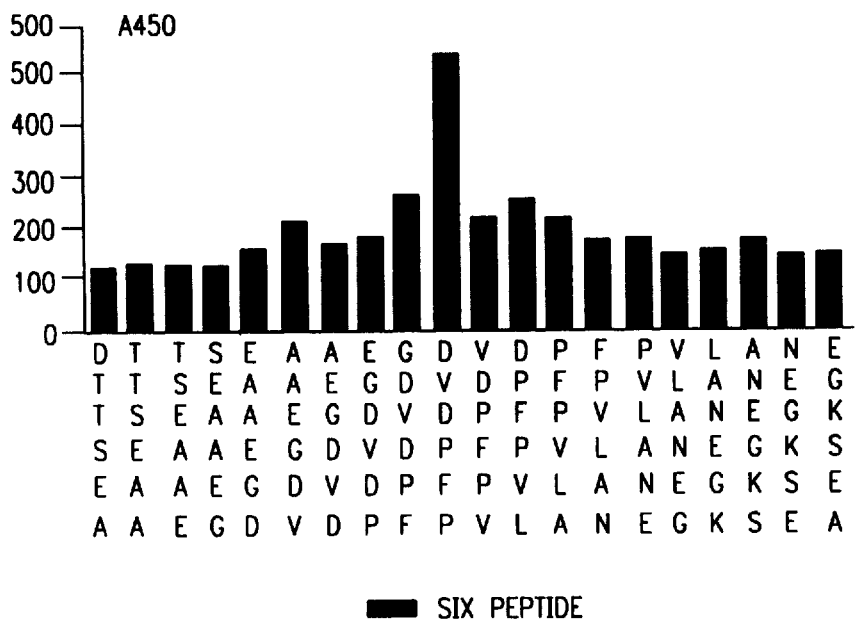
Figure 10E:
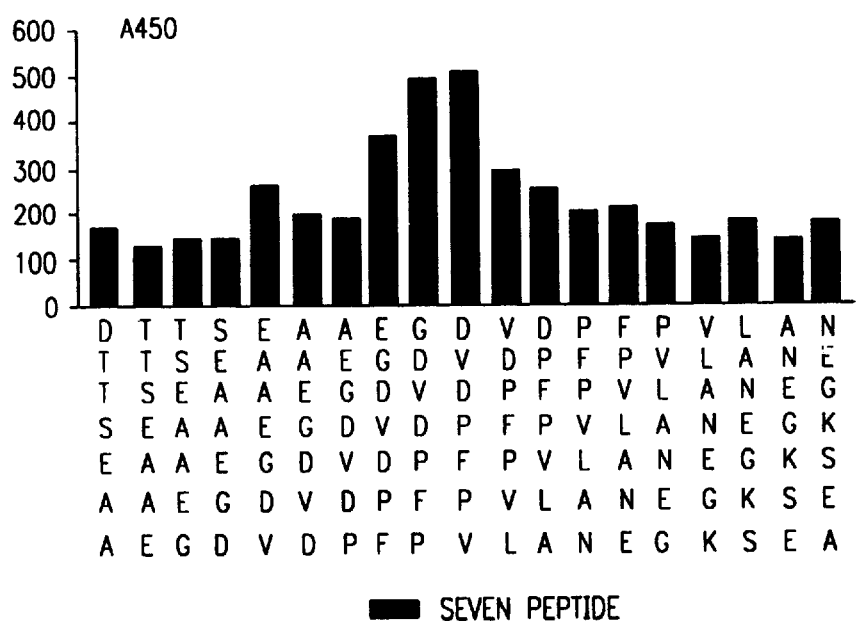
Figure 10F:
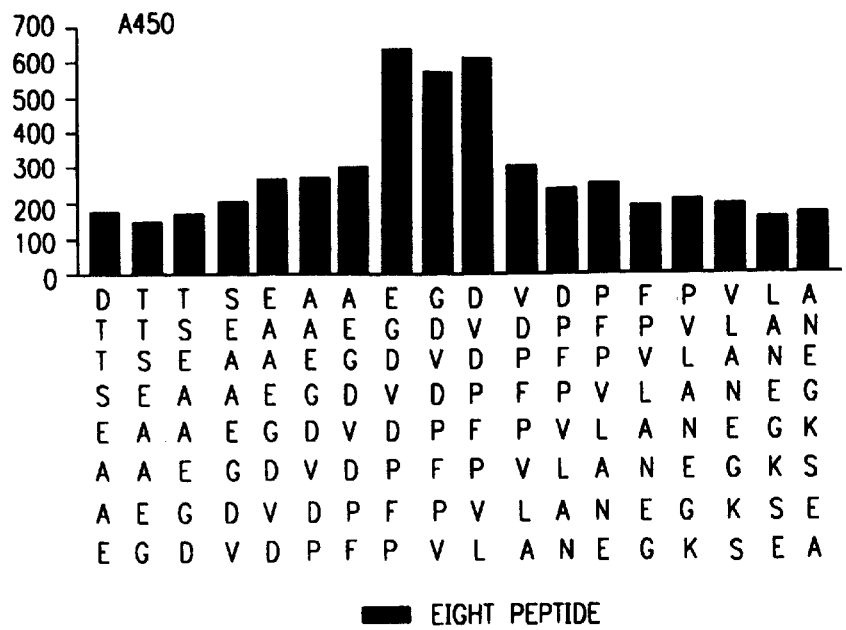
Figure 10G:
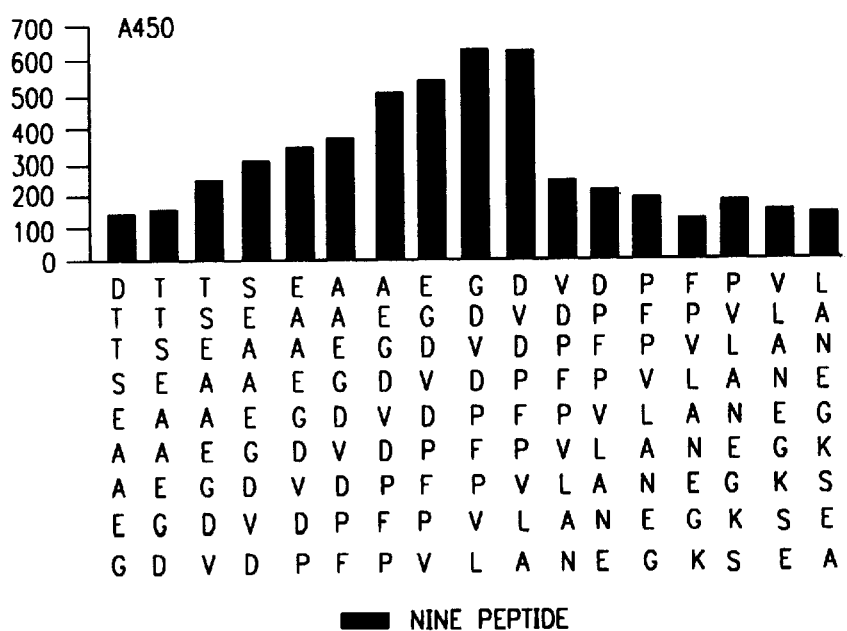
Figure 10H:
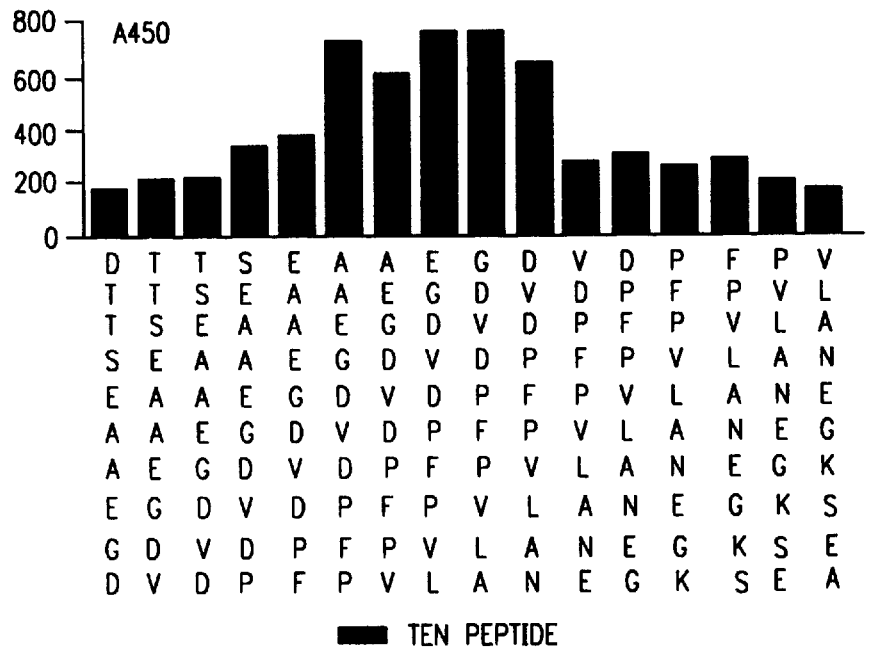
Figure 10I:
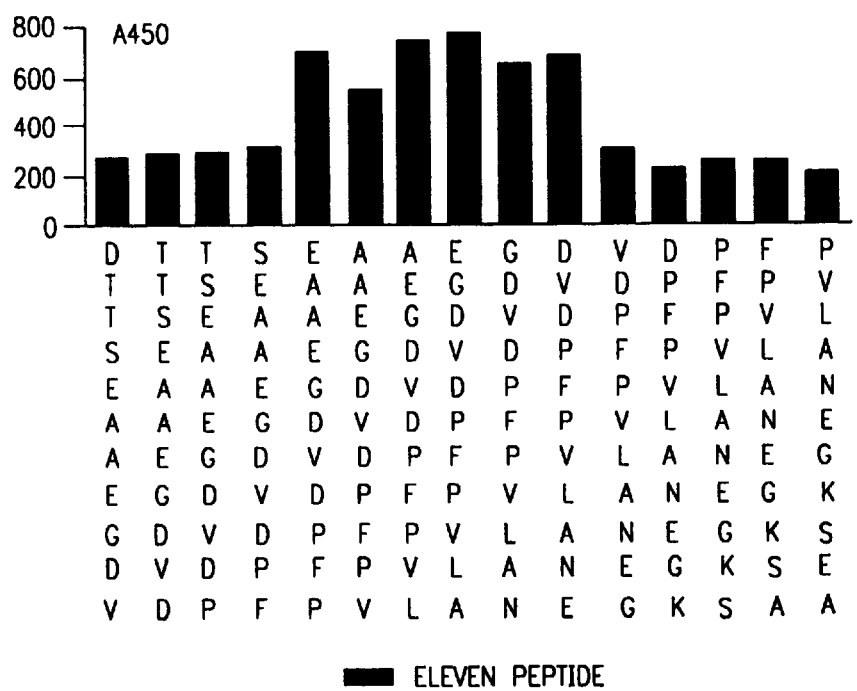
Figure 11:
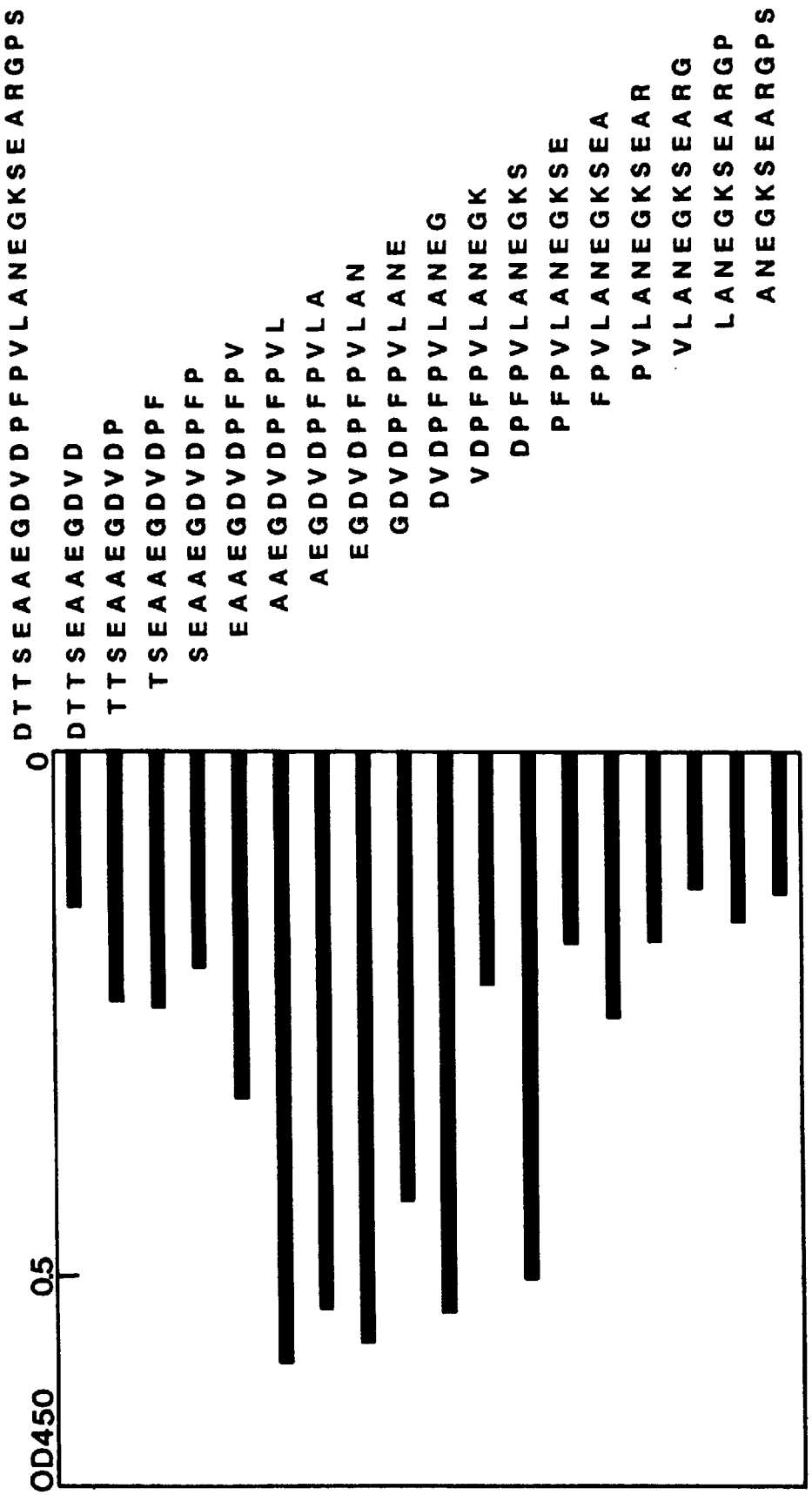
Figure 12:
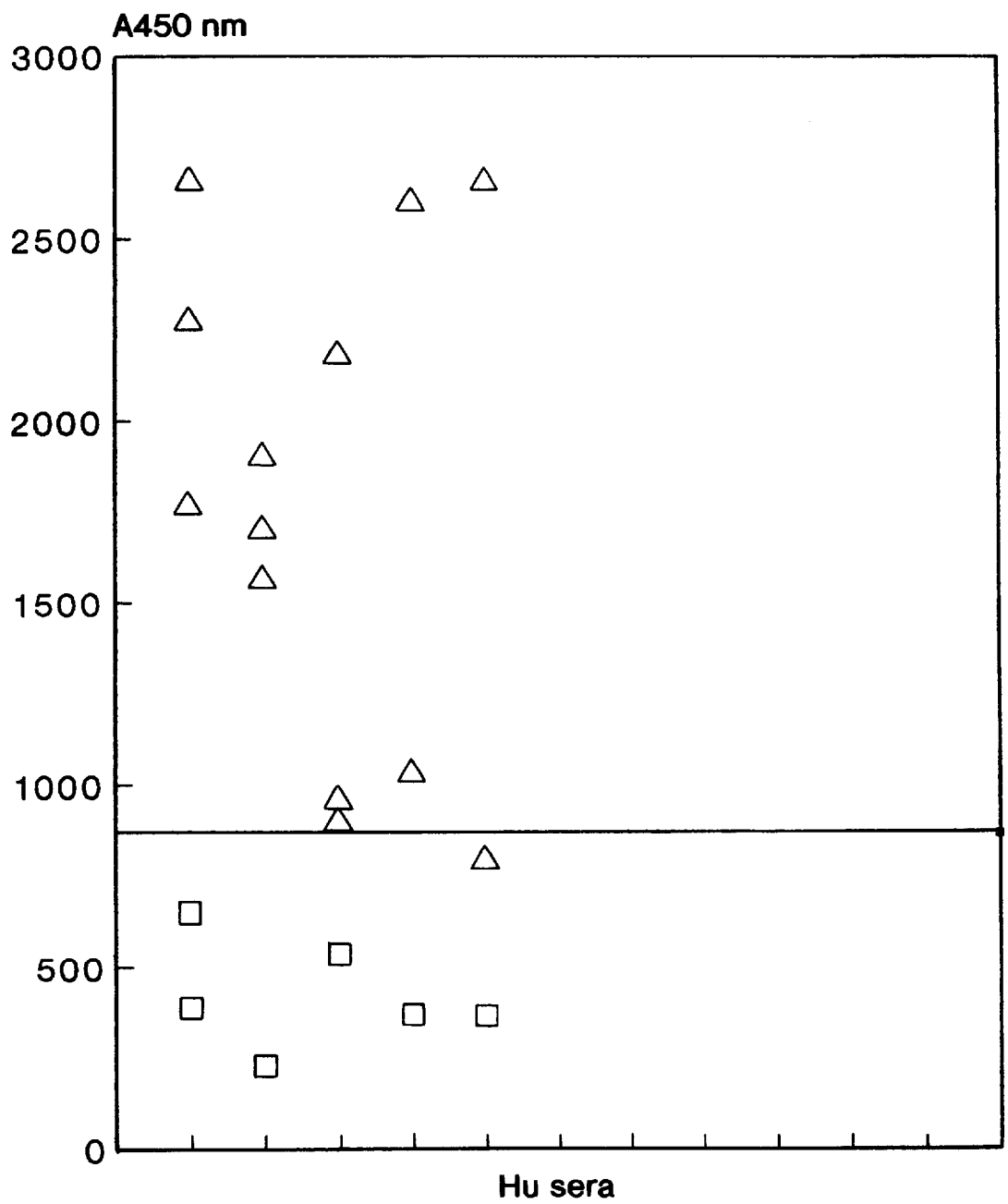
FIG. 12: ELISA results of synthetic peptide (SEQ ID No.: 3) example 10.

We claim:

1. A peptide immunoreactive with antibodies to *Toxoplamsa gondii*, wherein said peptide consisting of the amino acid sequence shown in SEQ ID NO:3 or 5.

2. An immunochemical reagent, comprising a peptide according to claim 1.

3. A test kit for the detection of *T. gondii*, comprising an immunochemical reagent according to claim 2.

4. A vaccine for protection against *Toxoplasma gondii*, comprising a peptide according to claim 1, together with a pharmaceutically acceptable carrier.

5. A fusion protein comprising two peptides, wherein the first peptide is a peptide consisting of SEQ ID NO: 3 or 5, and a second peptide which is a heterologous antigen.

6. A peptide in tendem repeats of a peptide consisting of the amino acid sequence of SEQ ID NO: 3 or 5.

* * * * *